US010189832B2

(12) United States Patent
Chen et al.

(10) Patent No.: US 10,189,832 B2
(45) Date of Patent: Jan. 29, 2019

(54) CRYSTALLINE SOLID FORMS OF A BET INHIBITOR

(71) Applicant: Incyte Corporation, Wilmington, DE (US)

(72) Inventors: Shili Chen, Newark, DE (US); Zhongjiang Jia, Kennett Square, PA (US); Pingli Liu, Newark, DE (US); Lei Qiao, Downingtown, PA (US); Yongzhong Wu, Glenn Mills, PA (US); Jiacheng Zhou, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/626,539

(22) Filed: Jun. 19, 2017

(65) Prior Publication Data
US 2017/0362229 A1 Dec. 21, 2017

Related U.S. Application Data

(60) Provisional application No. 62/397,575, filed on Sep. 21, 2016, provisional application No. 62/352,220, filed on Jun. 20, 2016.

(51) Int. Cl.
*C07D 471/04* (2006.01)
*C07F 5/02* (2006.01)
*C07D 471/02* (2006.01)

(52) U.S. Cl.
CPC ......... *C07D 471/04* (2013.01); *C07D 471/02* (2013.01); *C07F 5/025* (2013.01); *C07B 2200/13* (2013.01)

(58) Field of Classification Search
CPC .................................................. C07D 471/04
USPC .......................................................... 544/69
See application file for complete search history.

(56) References Cited

U.S. PATENT DOCUMENTS

| | | | |
|---|---|---|---|
| 5,589,476 A | 12/1996 | Jegham et al. | |
| 8,633,186 B2 | 1/2014 | Tachdjian et al. | |
| 8,669,249 B2 | 3/2014 | Brown et al. | |
| 9,012,642 B2 | 4/2015 | Haydar et al. | |
| 9,227,985 B2 | 1/2016 | Combs et al. | |
| 9,290,514 B2 | 3/2016 | Combs et al. | |
| 9,309,246 B2 | 4/2016 | Rodgers et al. | |
| 9,315,501 B2 | 4/2016 | Yue et al. | |
| 9,399,640 B2 | 7/2016 | Yue et al. | |
| 9,527,864 B2 | 12/2016 | Combs et al. | |
| 9,533,997 B2 | 1/2017 | Combs et al. | |
| 9,540,368 B2 | 1/2017 | Combs et al. | |
| 9,624,241 B2 | 4/2017 | Combs et al. | |
| 9,737,516 B2 | 8/2017 | Yue et al. | |
| 9,777,003 B2 | 10/2017 | Shepard et al. | |
| 9,834,565 B2 | 12/2017 | Combs et al. | |
| 9,850,257 B2 | 12/2017 | Combs et al. | |
| 9,918,990 B2 | 3/2018 | Yue et al. | |
| 9,938,294 B2 | 4/2018 | Combs et al. | |
| 9,957,628 B2 | 5/2018 | Combs et al. | |
| 2002/0004510 A1 | 1/2002 | McCall et al. | |
| 2007/0191447 A1 | 8/2007 | Kodo et al. | |
| 2007/0244096 A1 | 10/2007 | Fox et al. | |
| 2008/0306093 A1 | 12/2008 | Servant et al. | |
| 2009/0306122 A1 | 12/2009 | Staehle et al. | |
| 2013/0045229 A1 | 2/2013 | Iadonato et al. | |
| 2013/0261109 A1 | 10/2013 | Miyoshi et al. | |
| 2013/0281396 A1 | 10/2013 | McLure et al. | |
| 2013/0281397 A1 | 10/2013 | McLure et al. | |
| 2013/0281398 A1 | 10/2013 | McLure et al. | |
| 2013/0281399 A1 | 10/2013 | McLure et al. | |
| 2014/0135316 A1 | 5/2014 | Albrecht et al. | |
| 2014/0275030 A1 | 9/2014 | Combs et al. | |
| 2015/0011540 A1 | 1/2015 | Combs et al. | |
| 2015/0148342 A1 | 5/2015 | Yue et al. | |
| 2015/0148372 A1 | 5/2015 | Yue et al. | |
| 2015/0148375 A1 | 5/2015 | Yue et al. | |
| 2015/0175604 A1 | 6/2015 | Rodgers et al. | |
| 2015/0307493 A1 | 10/2015 | Combs et al. | |
| 2016/0046650 A1 | 2/2016 | Combs et al. | |
| 2016/0075721 A1 | 3/2016 | Combs et al. | |
| 2016/0159817 A1 | 6/2016 | Combs et al. | |
| 2016/0168148 A1 | 6/2016 | Shepard | |
| 2016/0213654 A1 | 7/2016 | Yue et al. | |
| 2016/0331749 A1 | 11/2016 | Bogdan et al. | |
| 2017/0014418 A1 | 1/2017 | Yue et al. | |
| 2017/0121347 A1 | 5/2017 | Chen et al. | |
| 2017/0158689 A1 | 6/2017 | Combs et al. | |
| 2017/0158710 A1 | 6/2017 | Combs et al. | |
| 2017/0210754 A1 | 7/2017 | Combs et al. | |
| 2017/0127985 A1 | 8/2017 | Combs et al. | |

FOREIGN PATENT DOCUMENTS

| | | |
|---|---|---|
| CA | 2171579 | 9/1996 |
| EP | 0646583 | 4/1995 |
| EP | 0 732 334 | 9/1996 |

(Continued)

OTHER PUBLICATIONS

Caira, "Crystalline Polymorphism of Organic Compounds," Topics in Current Chemistry, 1998, 198: 163-208.
Chinese Office Action in Chinese Application No. 201480025137, dated Oct. 13, 2017, 7 pages (English Translation).
International Search Report and Written Opinion in International Application No. PCT/US2017/038121, dated Oct. 20, 2017, 20 pages.

(Continued)

*Primary Examiner* — Kahsay Habte

(74) *Attorney, Agent, or Firm* — Fish & Richardson P.C.

(57) ABSTRACT

The present application relates to crystalline solid forms of an inhibitor of BET proteins such as BRD2, BRD3, BRD4, and BRD-t, including methods of preparation thereof, and intermediates in the preparation thereof, where the compound is useful in the treatment of diseases such as cancer.

38 Claims, 15 Drawing Sheets

(56) References Cited

FOREIGN PATENT DOCUMENTS

| | | |
|---|---|---|
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| KR | 20150037711 | 4/2015 |
| WO | WO 2002/000196 | 1/2002 |
| WO | WO 2004/024736 | 3/2004 |
| WO | WO 2005/080334 | 9/2005 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/013635 | 1/2015 |
| WO | WO 2015/081203 | 6/2015 |
| WO | WO 2015/095445 | 6/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2016/077378 | 5/2016 |
| WO | WO 2016/186453 | 11/2016 |
| WO | WO 2016/194806 | 12/2016 |
| WO | WO 2017/127930 | 8/2017 |
| WO | WO 2017/133681 | 8/2017 |

OTHER PUBLICATIONS

Ai et al., "Signal-induced Brd4 release from chromatin is essential for its role transition from chromatin targeting to transcriptional regulation," Nucleic Acids Res., 2011, 1-13.

Bamborough et al., "Fragment-Based Discovery of Bromodomain Inhibitors Part 2: Optimization of Phenylisoxazole Sulfonamides," J Med Chem., 2012, 55:587-596.

(56) References Cited

OTHER PUBLICATIONS

Bartholomeeusen et al., "BET bromodomain inhibition activates transcription via a transient release of P-TEFb from 7SK snRNP," JBC, 2012, 16 pages.
Bauer, "Pharmaceutical Solids—The Amorphous Phase," Journal of Validation Technology, Jan. 2009, 15(3): 63-68.
Belkina and Denis, "BET domain co-regulators in obesity inflammation and cancer," Nat Rev Cancer, Jul. 2012, 12:465-477.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization,"J Comb Chem., 2004, 6(6):874-883.
Blom, "Two-pump at-column-dilution configuration for preparative liquid chromatography-mass spectrometry," J Comb Chem., 2002, 4(4):295-301.
Byrn et al., "Pharmaceutical Solids: A Strategic Approach to Regulatory Considerations," Pharmaceutical Research, Jul. 1995, 12(7): 945-954.
Cheng et al., "Inhibition of BET Bromodomain Targets Genetically Diverse Glioblastoma," Clin Cancer Res 19:1748-1759, Feb. 2013.
Chiang, "Brd4 engagement from chromatin targeting to transcriptional regulation: selective contact with acetylated histone H3 and H4," Biology Reports, Dec. 2009, 1:98, 7 pages.
Chilean Office Action in Chilean Application No. 201502734, dated Jan. 18, 2017, 8 pages (English Translation).
Chinese Office Action in Chinese Application No. 201480025137, dated May 17, 2016, 14 pages (English Translation).
Chinese Office Action in Chinese Application No. 201480025137, dated Feb. 16, 2017, 21 pages (w/ English Translation).
Chung et al., "Discovery and Characterization of Small Molecule Inhibitors of the BET Family Bromodomains," J Med Chem., 2011, 54:3827-3838.
Chung et al., "Fragment-Based Discovery of Bromodomain Inhibitors Part 1. Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Colombian Office Action in Colombian Application No. 15-227. 987, dated Jun. 9, 2017, 5 pages.
Dawson et al., "Inhibition of BET recruitment to chromatin as an effective treatment for MLL-fusion leukaemia," Nature, 2011, 5 pages.
Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Draker et al., "A Combination of H2A.Z and H4 Acetylation Recruits Brd2 to Chromatin during Transcriptional Activation," PLoS Genet., Nov. 2012, 8(11):e1003047, 17 pages.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Eurasian Office Action in Eurasian Application No. 201692134, dated Jun. 6, 2017, 4 pages (English Translation).

Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Greenwald et al., "Eμ-BRD2 transgenic mice develop B-cell lymphoma and leukemia," Blood 103(4):1475-1484, Feb. 2004.
Hackam et al., JAMA, 296(14), 2006, 1731-1732.
Hewings et al., "3,5-Dimethylisoxazoles Act As Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscrpit).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
International Preliminary Report on Patentability in International Application No. PCT/US2014/045543, dated Jan. 21, 2016, 7 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.

(56) References Cited

OTHER PUBLICATIONS

International Search Report and Written Opinion in International Application No. PCT/US2014/071102, dated Feb. 13, 2015, 9 pages.
International Preliminary Report on Patentability in International Application No. PCT/US2014/027872, dated Sep. 24, 2015, 8 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
International Preliminary Report on Patentability in International Application No. PCT/US2015/027047, dated Oct. 25, 2016, 10 pages.
International Search Report and Written Opinion in International Application No. PCT/US2016/059360, dated Feb. 13, 2017, 20 pages.
Jang et al., "The bromodomain protein Brd4 is a positive regulatory component of P-TEFb and stimulates RNA polymerase II-dependent transcription," Mol. Cell, Aug. 2005, 19(4):523-534.
Japanese Office Action in Japanese Application No. 2016-502650, dated Jan. 10, 2017, 3 pages (English translation only).
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.

Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Puissant et al., "Targeting MYCN in Neuroblastoma by BET Bromodomain Inhibition," Cancer Discovery, 16 pages, Mar. 2013.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Shimamura et al., "Efficacy of BET Bromodomain Inhibition in Kras-Mutant Non-Small Cell Lung Cancer," Clin Cancer Res, 10 pages, 2013.
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Segura et al., "BRD4 Sustains Melanoma Proliferation and Represents a New Target for Epigenetic Therapy," Cancer Res 73:6264-6276, Aug. 2013.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "What do viruses BET on?" Frontiers Biosci., Jan. 2010, 15:537-549.

(56) References Cited

OTHER PUBLICATIONS

Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Wyce et al., "Inhibition of BET bromodomain proteins as a therapeutic approach in prostate cancer," Oncotarget, 13 pages, Nov. 2013.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavirus E2 protein with Brd4 tethers the viral DNA to host mitotic chromosomes," Cell, 2004, 117(3):349-60.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zhu et al., "Reactivation of latent HIV-1 by inhibition of BRD4," Cell Reports, 2012, 2(4):807-816.
Zuber et al., "An integrated approach to dissecting oncogene addiction implicates a Myb-coordinated self-renewal program as essential for leukemia maintenance," Genes Dev., 2011, 25:1628-1640.
Zuber et al., "RNAi screen identifies Brd4 as a therapeutic target in acute myeloid leukaemia," Nature, 2011, 478(7370):524-528.
Zuber et al., "Supplemental Information: RNAi screen identifies Brd4 as a therapeutic target in acute myeloid leukaemia," Nature, 2011, 33 pages.
Australian Office Action in Australian Application No. 2014228175, dated May 10, 2018, 4 pages.
Japanese Office Action in Japanese Application No. 2017-134538, dated Jun. 12, 2018, 7 pages (English Translation).
Japanese Office Action in Japanese Application No. 2016-525398, dated Mar. 15, 2018, 5 pages (English Translation).

XRPD

DSC

TGA

XRPD

XRPD Form VIII

XRPD Form IX

XRPD Form XIV

XRPD Form XV

CRYSTALLINE SOLID FORMS OF A BET INHIBITOR

FIELD OF THE INVENTION

The present application relates to crystalline solid forms of 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one, which is an inhibitor of BET proteins such as BRD2, BRD3, BRD4, and BRD-t, including methods of preparation thereof, and intermediates in the preparation thereof, where the compound is useful in the treatment of diseases such as cancer.

BACKGROUND OF THE INVENTION

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146:904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Inhibitors of BET proteins are in current development. Exemplary BET protein inhibitors are disclosed in, for example, U.S. Pat. App. Pub. Nos. 2014/0275030; 2015/0011540; 2015/0148375; 2015/0148342; 2015/0148372; 2015/0175604; and 2016/007572. In particular, the BET-inhibiting compound 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one is described in US 2015/0307493. For the development of a drug, it is typically advantageous to employ a form of the drug having desirable properties with respect to its preparation, purification, reproducibility, stability, bioavailability, and other characteristics. Accordingly, the solid crystalline forms of the compound provided herein help satisfy the ongoing need for the development of BET inhibitors for the treatment of diseases.

SUMMARY OF THE INVENTION

The present application provides, inter alia, crystalline solid forms of an inhibitor of a BET protein, wherein the inhibitor is 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one.

The present application also provides pharmaceutical compositions comprising a crystalline solid form of 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3 (4H)-one and at least one pharmaceutically acceptable carrier.

The present application also provides methods of using a crystalline solid form of 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one in the treatment of diseases and disorders associated with activity of BET proteins Further, the present application provides methods of preparing 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one and crystalline solid forms thereof.

Furthermore, the present application provides intermediate compounds, and methods for their preparation, useful in the synthesis of 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one.

The details of one or more embodiments are set forth in the description below. Other features, objects, and advantages will be apparent from the description and from the claims.

DETAILED DESCRIPTION

Figure 1:
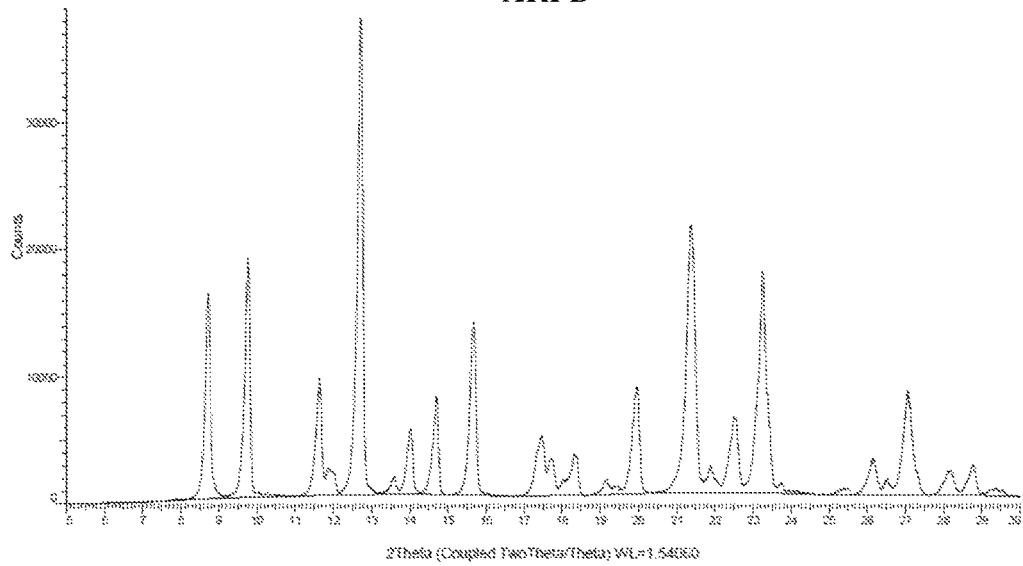
FIG. 1 is an X-ray powder diffraction (XRPD) pattern of Form I of Compound 1.

Crystalline Forms and Processes for their Preparation

The present application provides, inter alia, crystalline solid forms of an inhibitor of a BET protein, wherein the inhibitor is 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one (see below), referred to herein as "Compound 1":

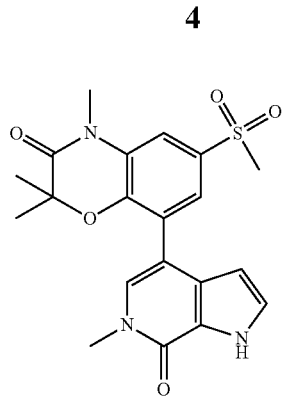

Compound 1

Typically, different crystalline forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage. Anhydrous forms are often desirable because they can be consistently made without concern for variation in weight or composition due to varying solvent or water content. On the other hand, hydrated or solvated forms can be advantageous in that they are less likely to be hygroscopic and may show improved stability to humidity under storage conditions.

The crystalline solid forms of the present invention can include solvent such as water (e.g., a hydrated form) or be substantially free of water and solvent (e.g., forming an anhydrate). In some embodiments, the crystalline solid form is an anhydrate. In further embodiments, the crystalline solid form is hydrated.

Compound 1 can be obtained in a solid crystalline form referred to as Form I, which is described below and in the Examples. Experimental data show that Form I is an anhydrate. Form I is characterized by its XRPD pattern and other solid state characteristics. In some embodiments, Form I has a characteristic XRPD peak, in terms of 2-theta, at about 12.7 degrees. In some embodiments, Form I has one or more characteristic XRPD peaks, in terms of 2-theta, selected from about 8.7, about 9.8, and about 12.7 degrees. In some embodiments, Form I has one or more characteristic XRPD peaks, in terms of 2-theta, selected from about 8.7, about 9.8, about 12.7, about 21.4, and about 23.3 degrees.

In some embodiments, Form I has two or more characteristic XRPD peaks, in terms of 2-theta, selected from about 8.7, about 9.8, about 12.7, about 21.4, and about 23.3 degrees.

In some embodiments, Form I has two or more characteristic XRPD peaks, in terms of 2-theta, selected from about 8.7, about 9.8, about 11.6, about 12.7, about 14.7, about 15.7, about 20.0, about 21.4, about 23.3, and about 27.1 degrees.

In some embodiments, Form I has three or more characteristic XRPD peaks, in terms of 2-theta, selected from about 8.7, about 9.8, about 11.6, about 12.7, about 14.7, about 15.7, about 20.0, about 21.4, about 23.3, and about 27.1 degrees.

In some embodiments, Form I has four or more characteristic XRPD peaks, in terms of 2-theta, selected from about 8.7, about 9.8, about 11.6, about 12.7, about 14.7, about 15.7, about 20.0, about 21.4, about 23.3, and about 27.1 degrees.

In some embodiments, Form I has an XRPD pattern substantially as shown in FIG. 1.

Figure 2:
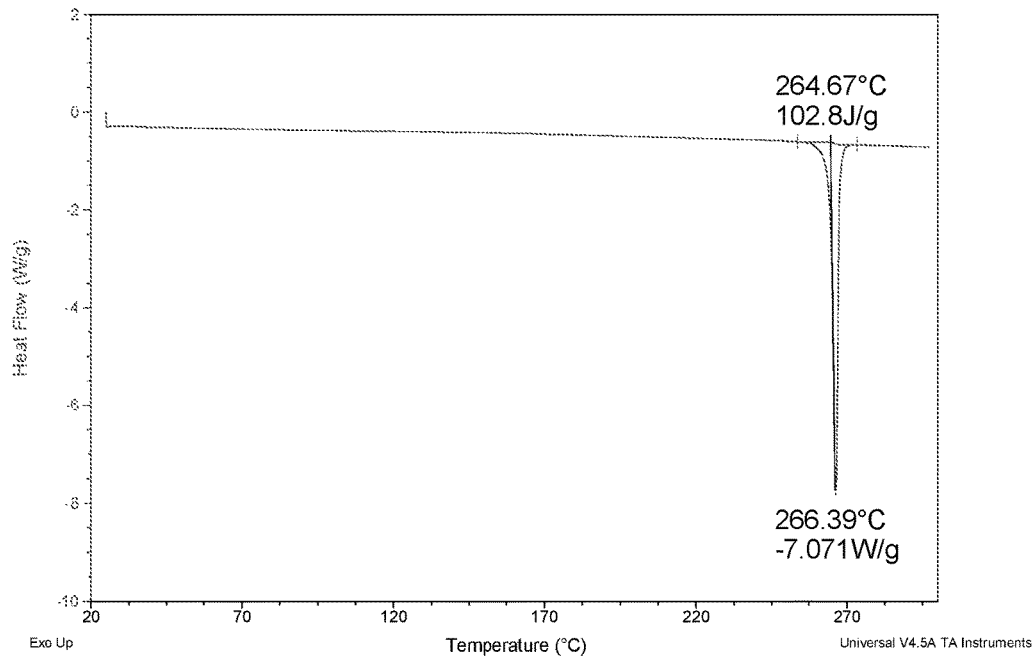
FIG. 2 is a differential scanning calorimetry (DSC) thermogram of Form I of Compound 1.

In some embodiments, Form I has a DSC thermogram characterized by an endothermic peak at a temperature of about 266° C. In some embodiments, Form I has a DSC thermogram substantially as shown in FIG. 2.

Figure 3:
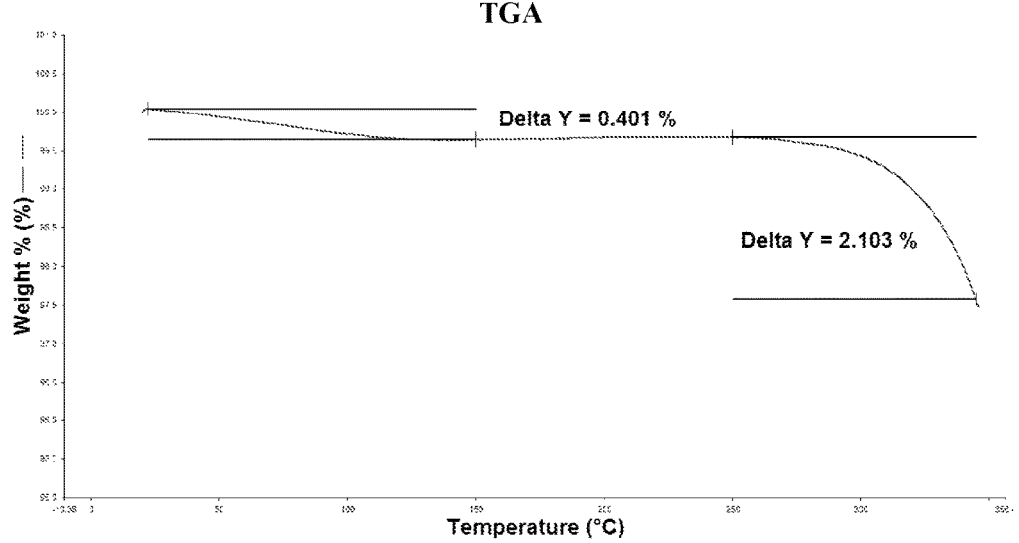
FIG. 3 is a thermogravimetric analysis (TGA) thermogram of Form I of Compound 1.

In some embodiments, Form I has a TGA thermogram substantially as shown in FIG. 3.

Form I can be generally prepared by precipitating Form I from a solution comprising Compound 1 and a solvent. In some embodiments, the solvent comprises methanol, acetone, n-heptane, or a mixture thereof. For example, Form 1 can be prepared by precipitating Form I from a solution comprising Compound I and acetone. The preparation of Form I can include adding Compound 1 to a saturated solution of Compound 1 in acetone and stirring the resulting solution at about 25° C. for about 3 days.

In some embodiments, the precipitating of Form I is carried out by (1) reducing the temperature of the solution of Compound 1 (e.g., the solution of Compound 1 at elevated temperature), (2) concentrating the solution of Compound 1, (3) adding an anti-solvent to the solution of Compound 1, or any combination thereof. In some embodiments, the precipitating is carried out by adding the anti-solvent to the solution of Compound 1, wherein said solution of Compound 1 comprises a protic solvent and an aprotic solvent. In some embodiments, the protic solvent is methanol, the aprotic solvent is acetone, and the anti-solvent is n-heptane. In some embodiments, the precipitating of Form I is carried out by adding n-heptane to the solution of Compound 1, wherein said solution of Compound 1 comprises a methanol and acetone.

In some embodiments, the preparation of Form I comprises:

(ia) heating the solution of Compound 1 to a temperature of about 50° C. to about 60° C.;

(iia) reducing the volume of the solution of Compound 1 at the temperature of about 50° C. to about 60° C. to form a reduced-volume solution of Compound 1;

(iiia) adding an anti-solvent to the reduced-volume solution of Compound 1 while maintaining the temperature at about 55° C. to about 65° C. to form a warm solution of Compound 1; and (iva) cooling the warm solution of Compound 1 to a temperature of about 15° C. to about 30° C. to precipitate Form I.

In some embodiments, the preparation of Form I comprises:

(ib) heating the solution of Compound 1, wherein the solution comprises methanol and acetone as solvent, to a temperature of about 50° C. to about 60° C.;

(iib) reducing the volume of the solution of Compound 1 at the temperature of about 50° C. to about 60° C. to form a reduced-volume solution of Compound 1;

(iiib) adding n-heptane to the reduced-volume solution of Compound 1 while maintaining the temperature at about 55° C. to about 65° C. to form a warm solution of Compound 1; and (ivb) cooling the warm solution of Compound 1 to a temperature of about 15° C. to about 30° C. to precipitate Form I.

Compound 1 can also be obtained as a crystalline form referred to as Form II, which is described below and in the Examples. Experimental data show that Form II is an anhydrate. Form II is characterized by its XRPD pattern and other solid state characteristics. In some embodiments, Form II has a characteristic XRPD peak, in terms of 2-theta, at about 17.0 degrees. In some embodiments, Form II has one or more characteristic XRPD peaks, in terms of 2-theta, selected from about 17.0 and about 19.3 degrees. In some embodiments, Form II has one or more characteristic XRPD peaks, in terms of 2-theta, selected from about 16.2, about 17.0, and about 19.3 degrees.

In some embodiments, Form II has two or more characteristic XRPD peaks, in terms of 2-theta, selected from about 6.7, about 9.5, about 10.5, about 14.8, about 16.2, about 17.0, about 18.8, and about 19.3 degrees.

In some embodiments, Form II has three or more characteristic XRPD peaks, in terms of 2-theta, selected from about 6.7, about 9.5, about 10.5, about 14.8, about 16.2, about 17.0, about 18.8, and about 19.3 degrees.

In some embodiments, Form II has four or more characteristic XRPD peaks, in terms of 2-theta, selected from about 6.7, about 9.5, about 10.5, about 14.8, about 16.2, about 17.0, about 18.8, and about 19.3 degrees.

Figure 4:
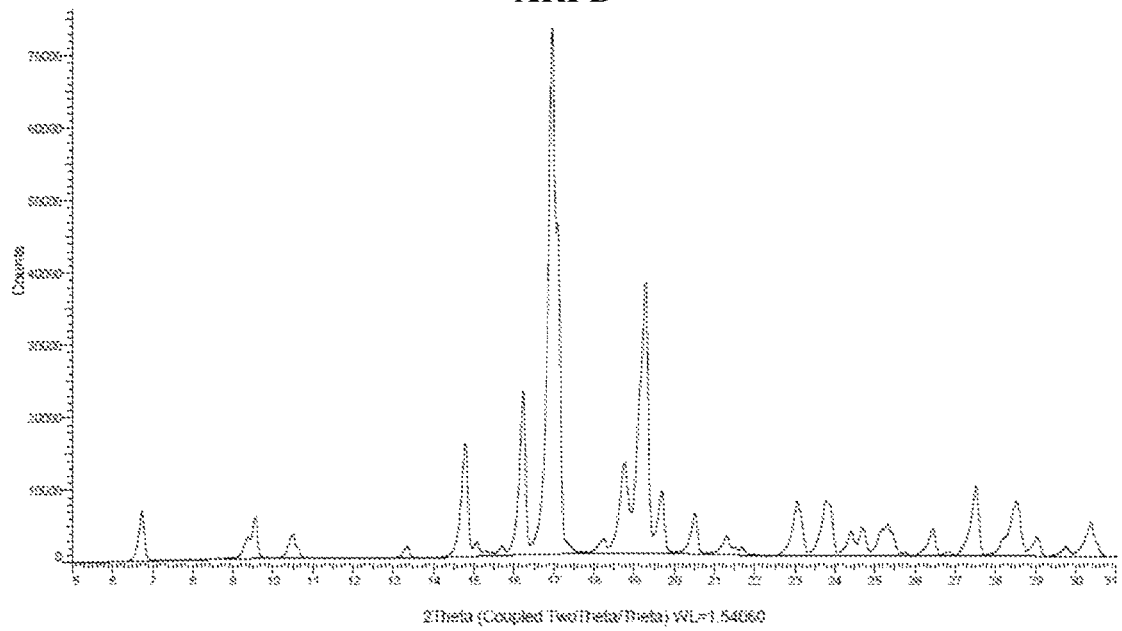
FIG. 4 is an XRPD pattern of Form II of Compound 1.

In some embodiments, Form II has an XRPD pattern substantially as shown in FIG. 4.

Figure 5:
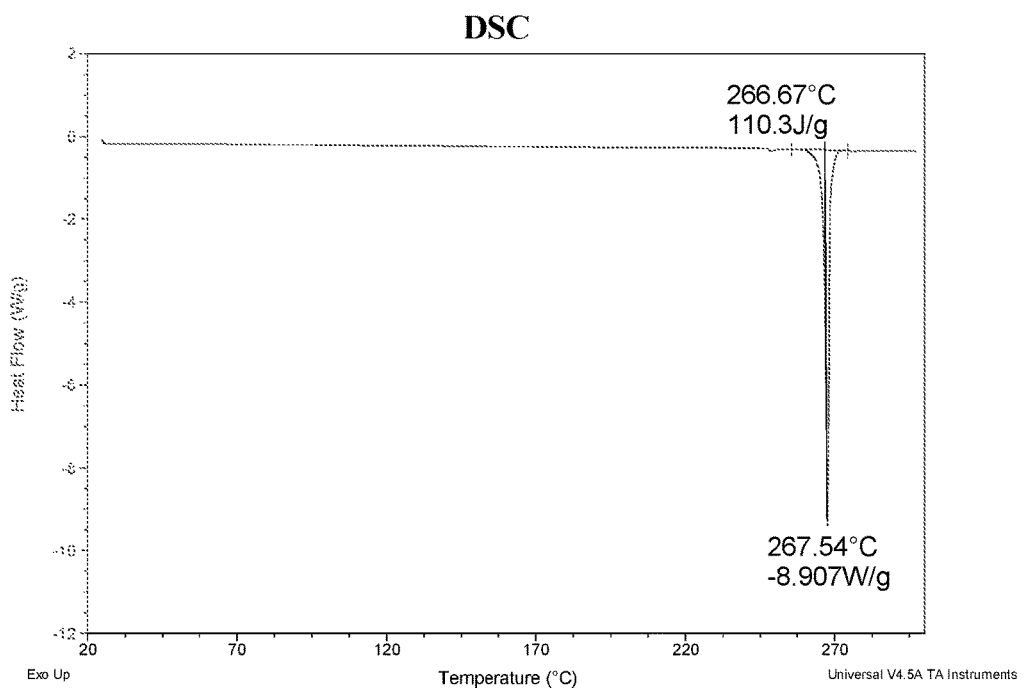
FIG. 5 is a DSC thermogram of Form II of Compound 1.

In some embodiments, Form II has a DSC thermogram characterized by an endothermic peak at a temperature of about 268° C. In some embodiments, Form II has a DSC thermogram substantially as shown in FIG. 5.

Figure 6:
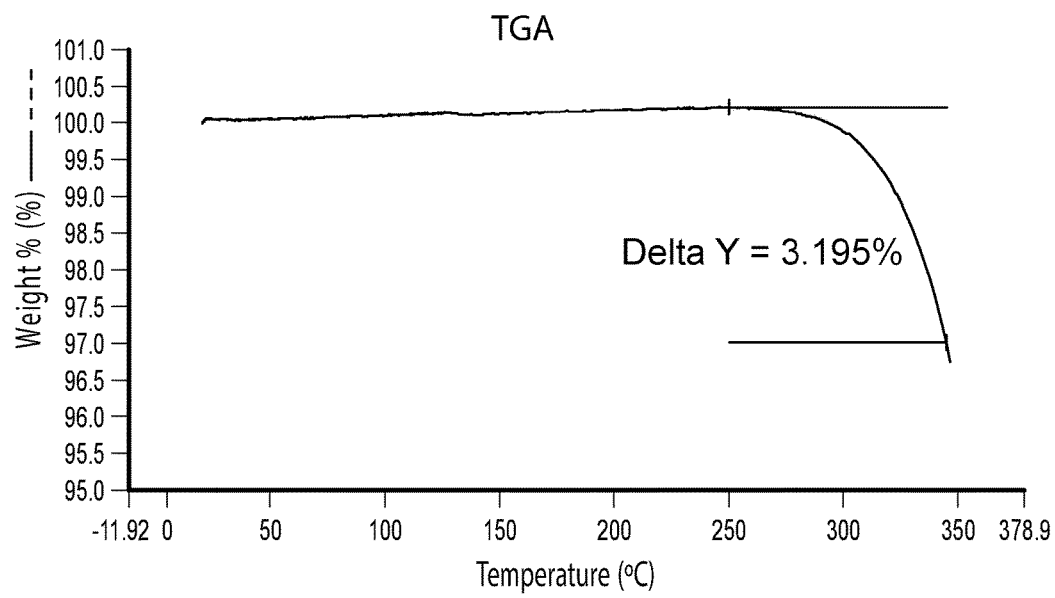
FIG. 6 is a TGA thermogram of Form II of Compound 1.

In some embodiments, Form II has a TGA thermogram substantially as shown in FIG. 6.

Form II can be generally prepared by precipitating Form II from a solution comprising Compound I and a solvent. In some embodiments, the solvent comprises tetrahydrofuran (THF), acetone, n-heptane, or a mixture thereof. In some embodiments, the precipitating of Form II is carried out (1) reducing the temperature of the solution of Compound 1, (2) concentrating the solution of Compound 1, (3) adding an anti-solvent to the solution of Compound 1, or any combinations thereof. In some embodiments, the precipitating of Form II is carried out by adding the anti-solvent to the solution of Compound 1, wherein said solution comprises an ether solvent and an aprotic solvent. In some embodiments, the ether solvent is THF, the aprotic solvent is acetone, and the anti-solvent is n-heptane. In some embodiments, the precipitating of Form II is carried out by adding n-heptane to the solution of Compound 1, wherein said solution of Compound 1 comprises THF and acetone.

In some embodiments, the preparation of Form II comprises:

(ic) heating the solution of Compound 1 to a temperature of about 50° C. to about 60° C.;

(iic) reducing the volume of the solution of Compound 1 at the temperature of about 50° C. to about 60° C. to form a reduced-volume solution of Compound 1;

(iiic) adding an anti-solvent to the reduced-volume solution of Compound 1 while maintaining the temperature at about 55° C. to about 65° C. to form a warm solution of Compound 1; and (ivc) cooling the warm solution of Compound 1 to a temperature of about 15° C. to about 30° C. to precipitate Form II.

In some embodiments, the preparation of Form II comprises:

(id) heating the solution of Compound 1, wherein the solution comprises THF and acetone as solvent, to a temperature of about 50° C. to about 60° C.;

(iid) reducing the volume of the solution of Compound 1 at a temperature of about 50° C. to about 60° C. to form a reduced-volume solution of Compound 1;

(iiid) adding n-heptane to the reduced-volume solution of Compound 1 while maintaining the temperature at about 55° C. to about 65° C. to form a warm solution of Compound 1; and (ivd) cooling the warm solution of Compound 1 to a temperature of about 15° C. to about 30° C. to precipitate Form II.

Compound 1 can also be obtained in solid crystalline forms referred to as Forms Ia, III, IV, V, Va, VI, VII, VIII, IX, X, XI, XII, XIII, XIV, and XV, which are described below and in the Examples. Forms Ia, III, IV, V, Va, VI, VII, VIII, IX, X, XI, XII, XIII, XIV, and XV are characterized by their XRPD pattern and other solid state characteristics.

Figure 7:
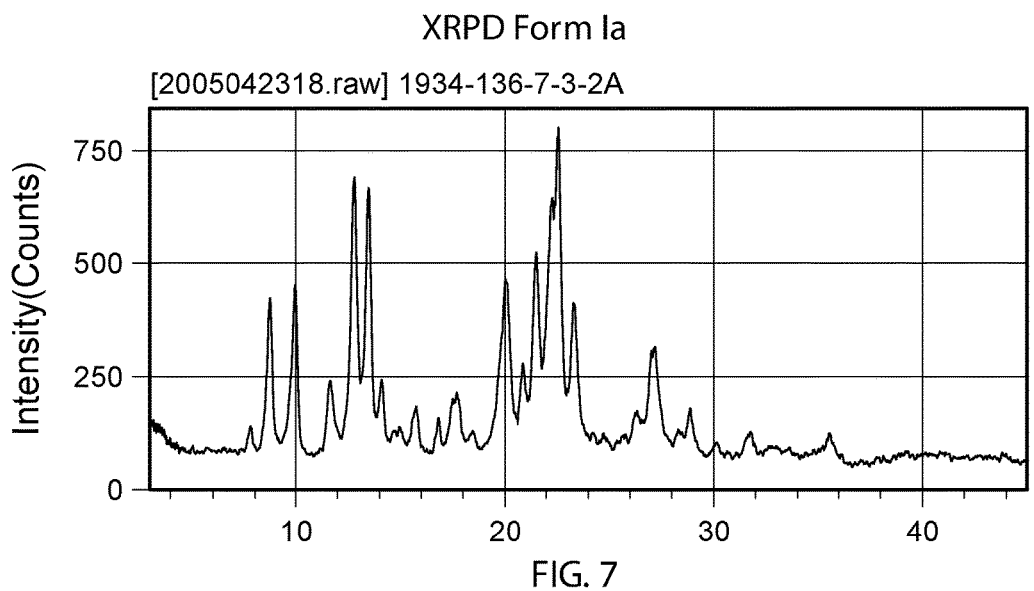
FIG. 7 is an XRPD pattern of Form Ia of Compound 1.

In some embodiments, Form Ia has one or more characteristic XRPD peaks, in terms of 2-theta, selected from about 8.8, about 10.0, about 11.7, about 12.8, and about 13.5 degrees. In some embodiments, Form Ia has one or more characteristic XRPD peaks, in terms of 2-theta, selected from about 8.8, about 10.0, about 11.7, about 12.8, about 13.5, about 20.0, about 21.5, about 22.6, and about 23.3 degrees. In some embodiments, Form Ia has an XRPD pattern substantially as shown in FIG. 7.

Figure 8:
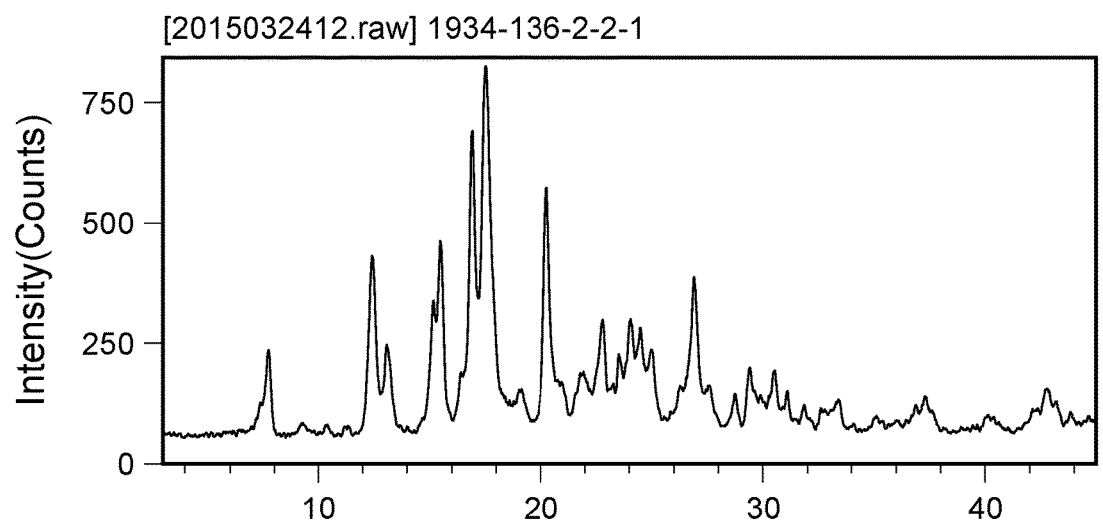
FIG. 8 is an XRPD pattern of Form III of Compound 1.

In some embodiments, Form III has one or more characteristic XRPD peaks, in terms of 2-theta, selected from about 7.8, about 12.4, about 13.1, about 15.2, and about 15.5 degrees. In some embodiments, Form III has one or more characteristic XRPD peaks, in terms of 2-theta, selected from about 7.8, about 12.4, about 13.1, about 15.2, about 15.5, about 16.9, about 17.5, and about 20.3 degrees. In some embodiments, Form III has an XRPD pattern substantially as shown in FIG. 8.

Figure 9:
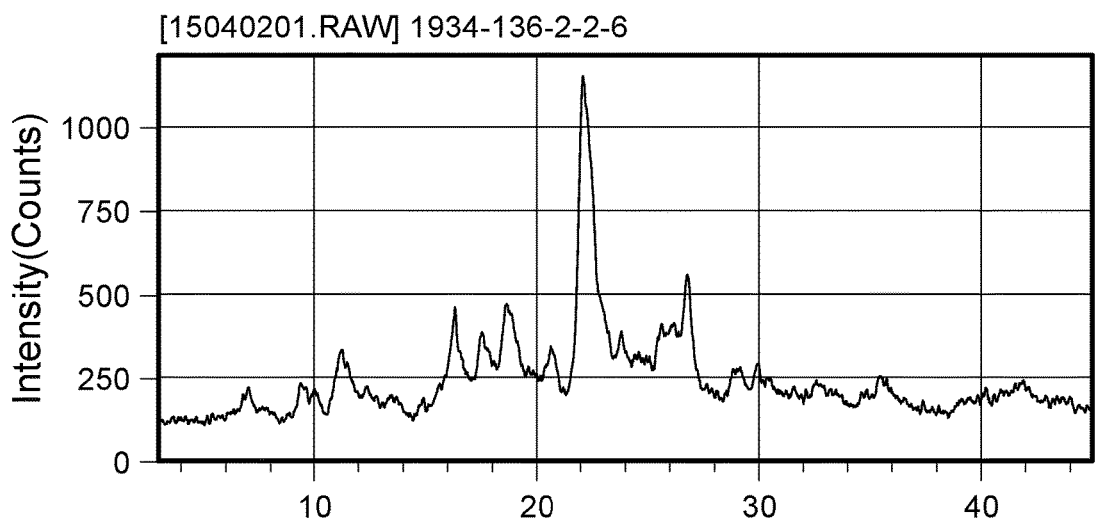
FIG. 9 is an XRPD pattern of Form IV of Compound 1.

In some embodiments, Form IV has one or more characteristic XRPD peaks, in terms of 2-theta, selected from about 11.2, about 16.3, about 18.7, and about 22.1 degrees. In some embodiments, Form IV has an XRPD pattern substantially as shown in FIG. 9.

Figure 10:
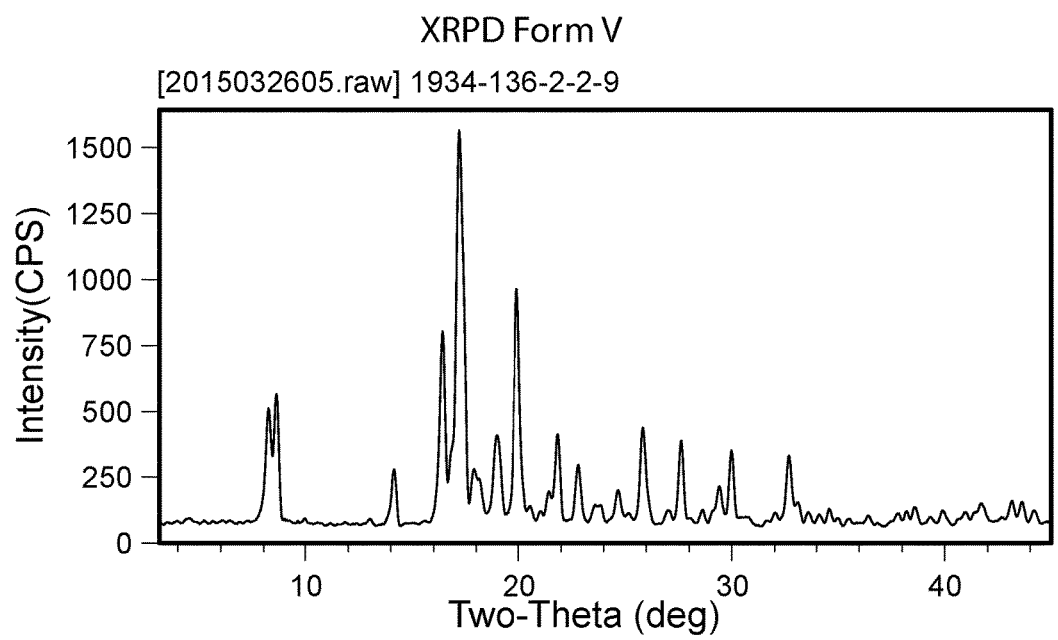
FIG. 10 is an XRPD pattern of Form V of Compound 1.

In some embodiments, Form V has one or more characteristic XRPD peaks, in terms of 2-theta, selected from about 8.2, about 8.5, about 14.1, about 16.3, and about 17.1 degrees. In some embodiments, Form V has one or more characteristic XRPD peaks, in terms of 2-theta, selected from about 8.2, about 8.5, about 14.1, about 16.3, about 17.1, about 18.9, about 19.8, about 21.8, and about 22.7 degrees. In some embodiments, Form V has an XRPD pattern substantially as shown in FIG. 10.

Figure 11:
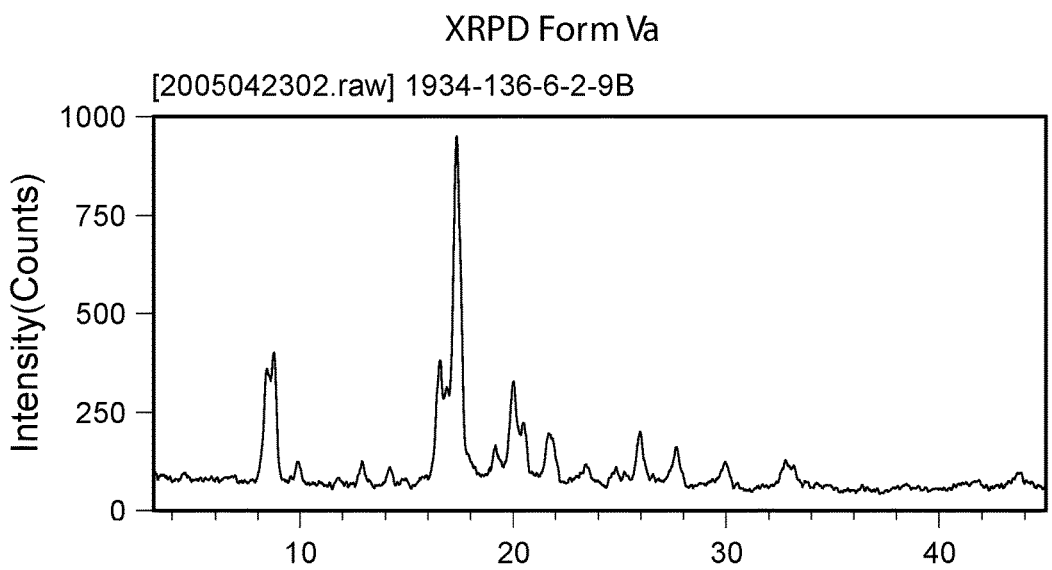
FIG. 11 is an XRPD pattern of Form Va of Compound 1.

In some embodiments, Form Va has one or more characteristic XRPD peaks, in terms of 2-theta, selected from about 8.7, about 16.5, about 17.3, about 19.9, and about 21.6 degrees. In some embodiments, Form Va has an XRPD pattern substantially as shown in FIG. 11. In some embodiments, Form Va has a DSC thermogram characterized by an endothermic peak at a temperature of about 133° C., an endothermic peak at a temperature of about 267° C., or a combination thereof.

Figure 12:
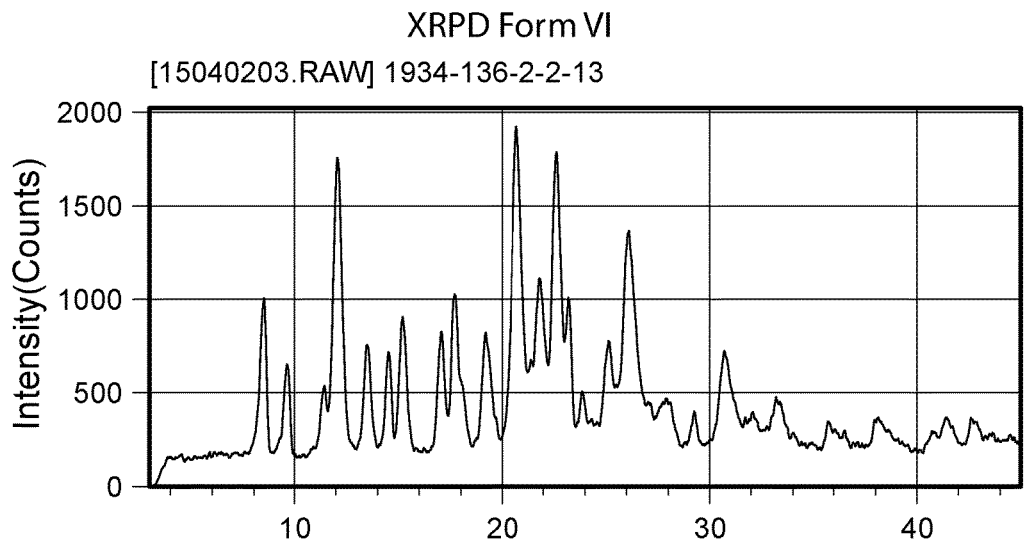
FIG. 12 is an XRPD pattern of Form VI of Compound 1.

In some embodiments, Form VI has one or more characteristic XRPD peaks, in terms of 2-theta, selected from about 8.5, about 9.6, about 11.4, and about 12.1 degrees. In some embodiments, Form VI has one or more characteristic XRPD peaks, in terms of 2-theta, selected from about 8.5, about 9.6, about 11.4, about 12.1, about 13.5, about 14.5, about 15.2, about 17.1, about 17.7, about 18.1, about 19.2, and about 20.7 degrees. In some embodiments, Form VI has an XRPD pattern substantially as shown in FIG. 12.

Figure 13:
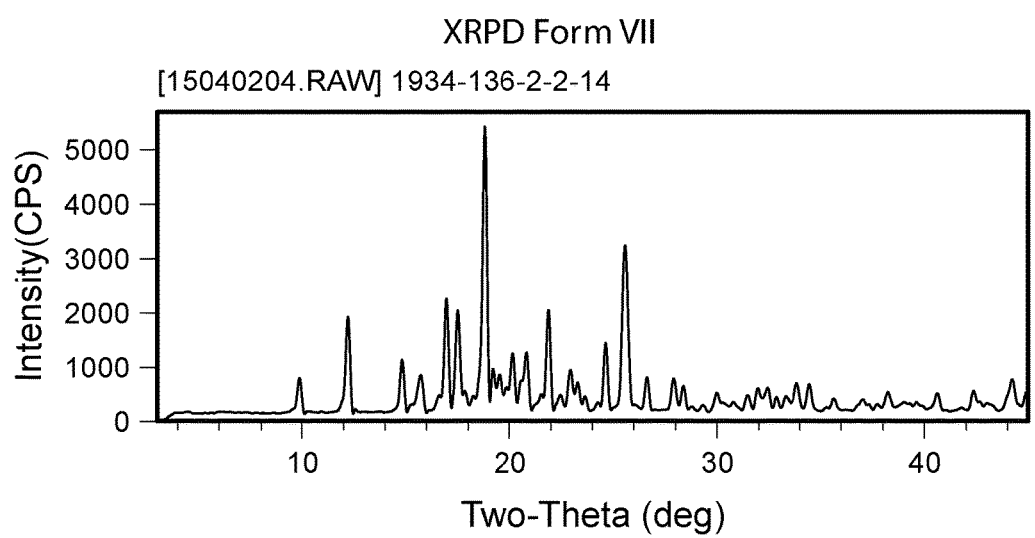
FIG. 13 is an XRPD pattern of Form VII of Compound 1.

In some embodiments, Form VII has one or more characteristic XRPD peaks, in terms of 2-theta, selected from about 9.9, about 12.2, about 14.8, and about 15.7 degrees. In some embodiments, Form VII has one or more characteristic XRPD peaks, in terms of 2-theta, selected from about 9.9, about 12.2, about 14.8, about 15.7, about 17.0, about 17.5, and about 18.8 degrees. In some embodiments, Form VII has an XRPD pattern substantially as shown in FIG. 13. In some embodiments, Form VII has a DSC thermogram characterized by an endothermic peak at a temperature of about 126° C., an endothermic peak at a temperature of about 256° C., an exothermic peak at a temperature of about 260° C., an endothermic peak at a temperature of about 267° C., or a combination thereof.

Figure 14:
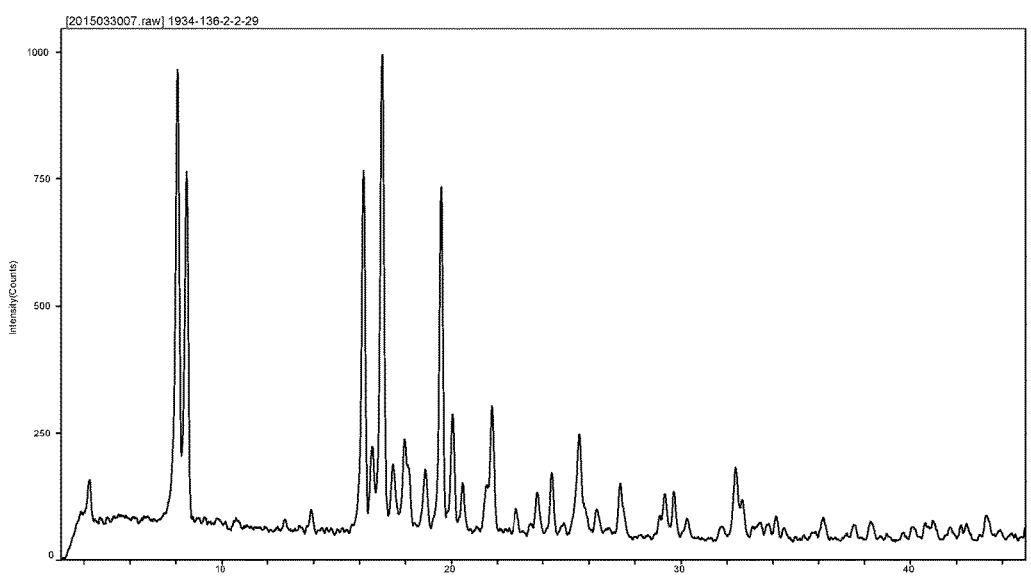
FIG. 14 is an XRPD pattern of Form VIII of Compound 1.

In some embodiments, Form VIII has one or more characteristic XRPD peaks, in terms of 2-theta, selected from about 8.1, about 8.5, about 16.2, and about 17.0 degrees. In some embodiments, Form VIII has one or more characteristic XRPD peaks, in terms of 2-theta, selected from about 8.1, about 8.5, about 16.2, about 16.6, about 17.0, about 17.5, about 18.0, about 18.9, about 19.6, and about 20.1 degrees. In some embodiments, Form VIII has an XRPD pattern substantially as shown in FIG. 14. In some embodiments, Form VIII has a DSC thermogram characterized by an endothermic peak at a temperature of about 145° C., an endothermic peak at a temperature of about 265° C., or a combination thereof.

Figure 15:
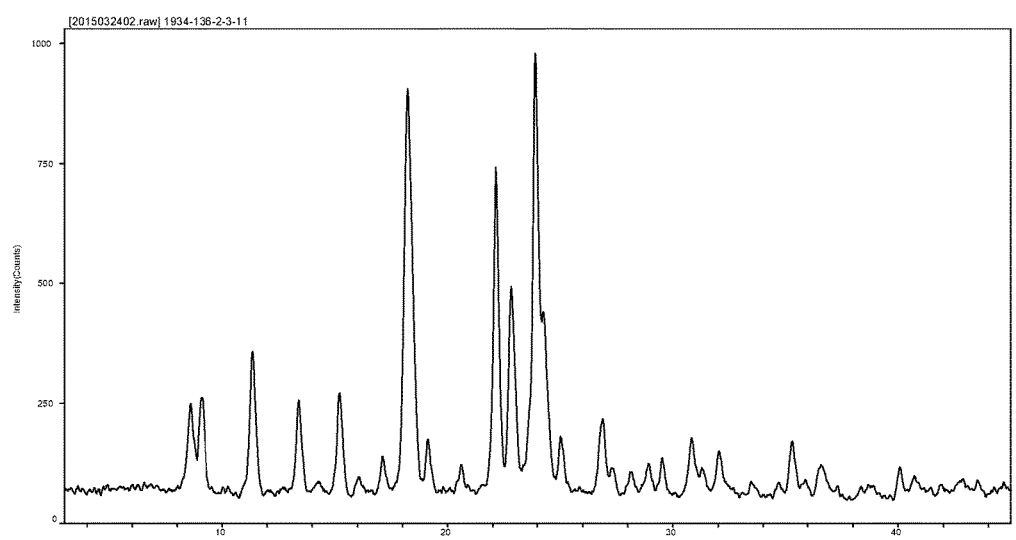
FIG. 15 is an XRPD pattern of Form IX of Compound 1.

In some embodiments, Form IX has one or more characteristic XRPD peaks, in terms of 2-theta, selected from about 8.6, about 9.1, about 11.4, about 13.4, and about 15.2 degrees. In some embodiments, Form IX has one or more characteristic XRPD peaks, in terms of 2-theta, selected from about 8.6, about 9.1, about 11.4, about 13.4, about 15.2, about 18.2, about 22.1, about 22.8, and about 23.9 degrees. In some embodiments, Form IX has an XRPD pattern substantially as shown in FIG. 15.

Figure 16:
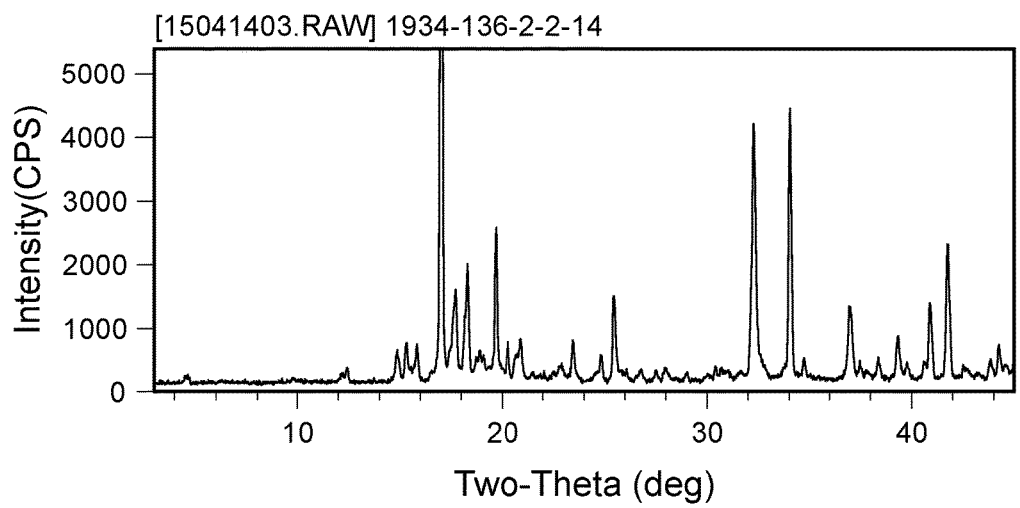
FIG. 16 is an XRPD pattern of Form X of Compound 1.

In some embodiments, Form X has one or more characteristic XRPD peaks, in terms of 2-theta, selected from about 14.9, about 15.3, about 15.8, and about 17.0 degrees. In some embodiments, Form X has one or more characteristic XRPD peaks, in terms of 2-theta, selected from about 14.9, about 15.3, about 15.8, about 17.0, about 17.7, about 18.3, and about 19.7 degrees. In some embodiments, Form X has an XRPD pattern substantially as shown in FIG. 16. In some embodiments, Form X has a DSC thermogram characterized by an endothermic peak at a temperature of about 121° C., an endothermic peak at a temperature of about 267° C., or a combination thereof.

Figure 17:
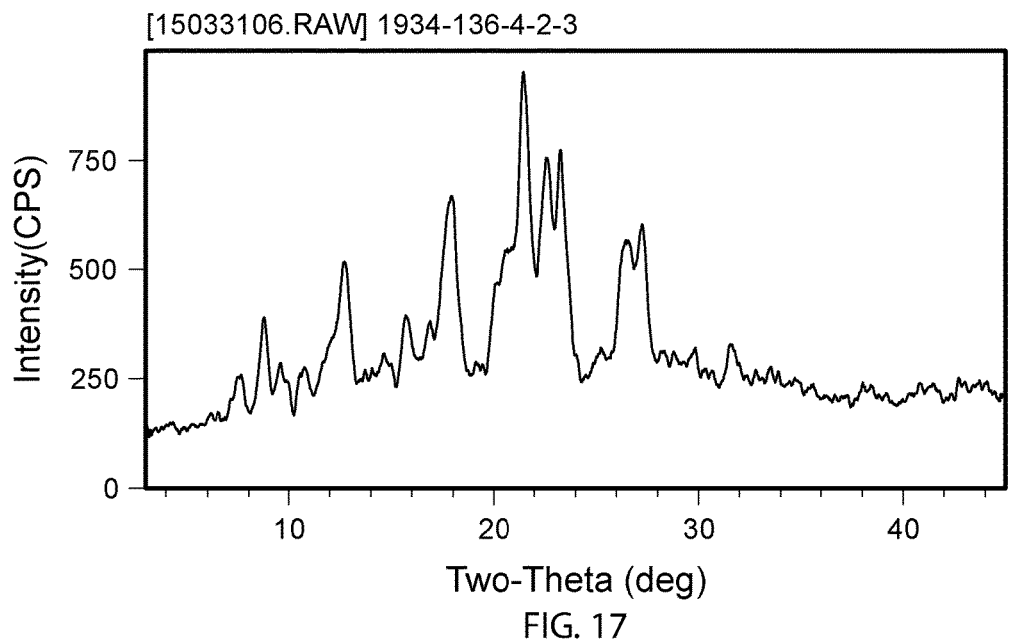
FIG. 17 is an XRPD pattern of Form XI of Compound 1.

In some embodiments, Form XI has one or more characteristic XRPD peaks, in terms of 2-theta, selected from about 8.9, about 12.8, about 18.0 about 21.5, about 22.6, and about 23.3 degrees. In some embodiments, Form XI has an XRPD pattern substantially as shown in FIG. 17.

Figure 18:
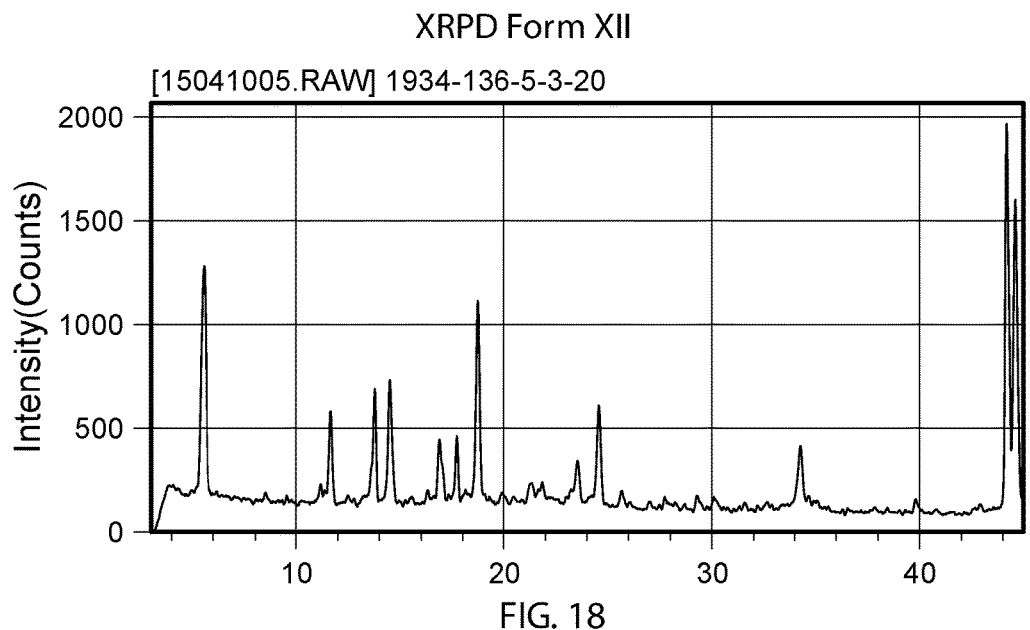
FIG. 18 is an XRPD pattern of Form XII of Compound 1.

In some embodiments, Form XII has one or more characteristic XRPD peaks, in terms of 2-theta, selected from about 5.6, about 11.7, about 13.8, and about 14.5 degrees. In some embodiments, Form XII has one or more characteristic XRPD peaks, in terms of 2-theta, selected from about 5.6, about 11.7, about 13.8, about 14.5, about 16.9, about 17.7, and about 18.7 degrees. In some embodiments, Form XII has one or more characteristic XRPD peaks, in terms of 2-theta, selected from about 5.6, about 11.7, about 13.8, about 14.5, about 16.9, about 17.7, about 18.7, about 23.5, about 24.6, about 34.3, about 44.2, and 44.6 degrees. In some embodiments, Form XII has an XRPD pattern substantially as shown in FIG. 18. In some embodiments, Form XII has a DSC thermogram characterized by an endothermic peak at a temperature of about 264° C.

Figure 19:
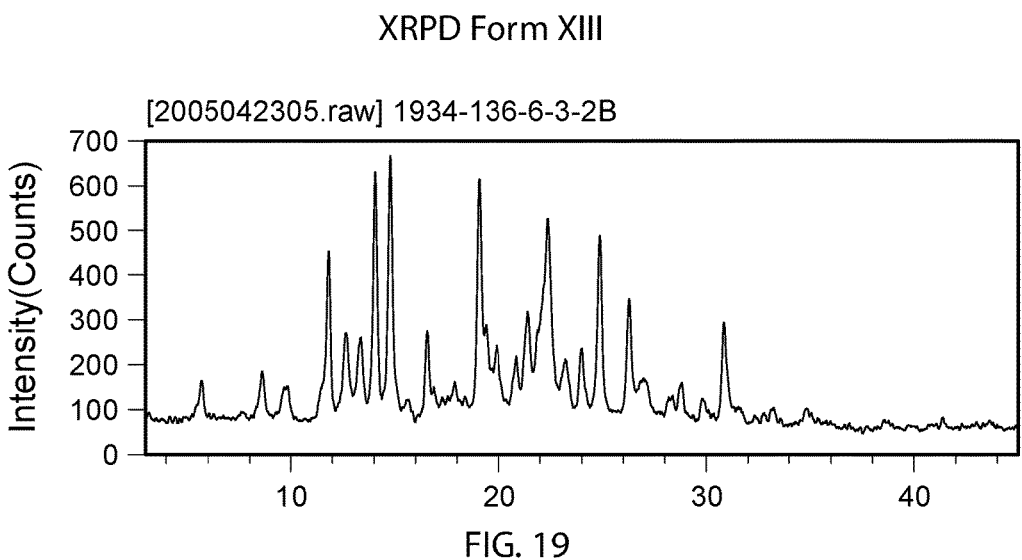
FIG. 19 is an XRPD pattern of Form XIII of Compound 1.

In some embodiments, Form XIII has one or more characteristic XRPD peaks, in terms of 2-theta, selected from about 5.7, about 8.6, about 9.8, and about 11.8 degrees. In some embodiments, Form XIII has one or more characteristic XRPD peaks, in terms of 2-theta, selected from about 5.7, about 8.6, about 9.8, about 11.8, about 12.6, about 13.4, about 14.1, about 14.8, about 16.6, and about 19.1 degrees. In some embodiments, Form XIII has an XRPD pattern substantially as shown in FIG. 19. In some embodiments, Form XIII has a DSC thermogram characterized by an endothermic peak at a temperature of 267° C.

Figure 20:
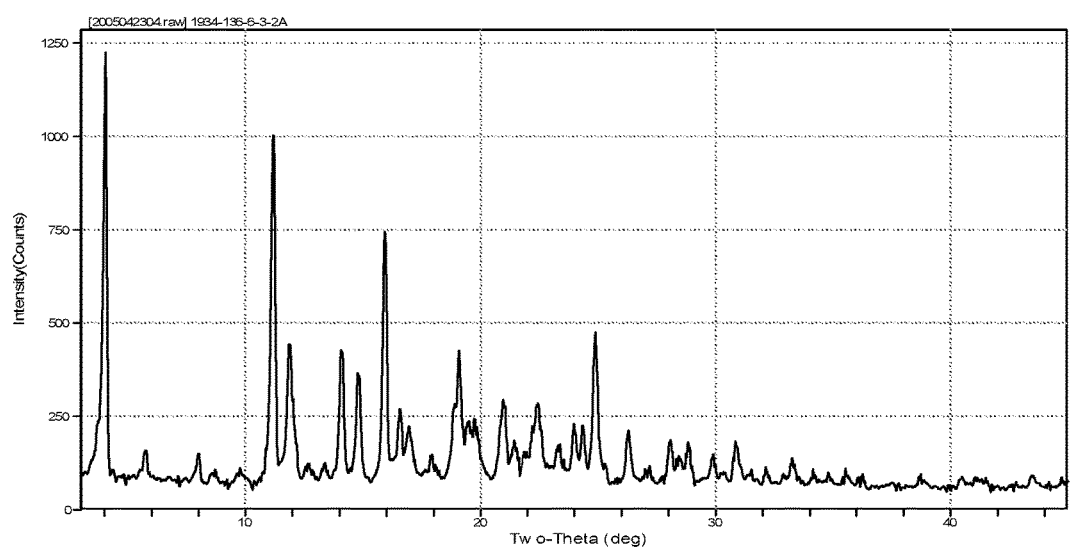
FIG. 20 is an XRPD pattern of Form XIV of Compound 1.

In some embodiments, Form XIV has one or more characteristic XRPD peaks, in terms of 2-theta, selected from about 4.0, about 11.2, about 11.9, about 14.1, about 14.8, and about 15.9 degrees. In some embodiments, Form XIV has an XRPD pattern substantially as shown in FIG. 20. In some embodiments, Form XIV has a DSC thermogram characterized by an endothermic peak at a temperature of 267° C.

Figure 21:
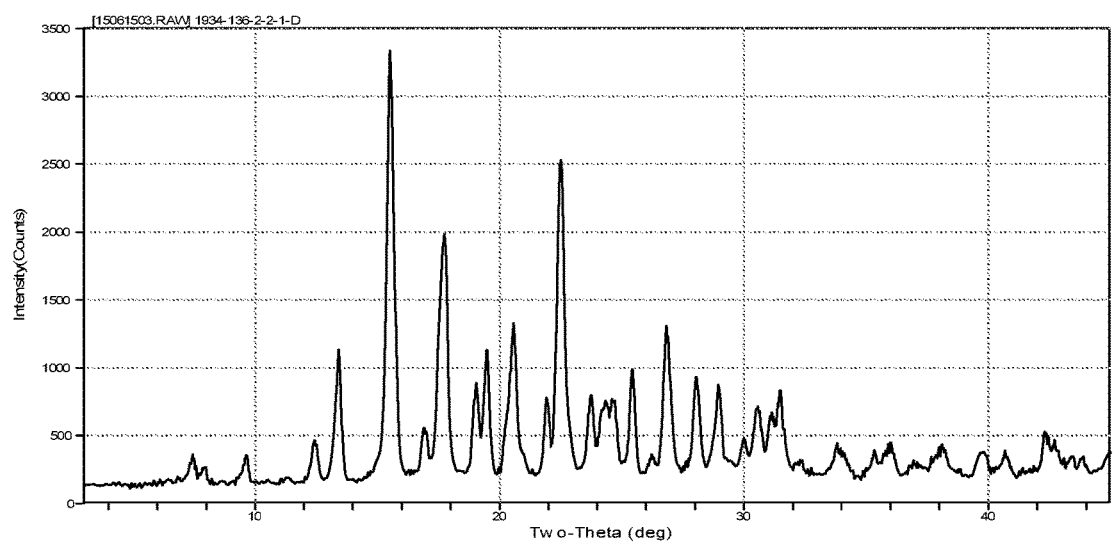
FIG. 21 is an XRPD pattern of Form XV of Compound 1.

In some embodiments, Form XV has one or more characteristic XRPD peaks, in terms of 2-theta, selected from about 7.4, about 9.6, about 12.4, about 13.4, and about 15.5 degrees. In some embodiments, Form XV has one or more characteristic XRPD peaks, in terms of 2-theta, selected from about 7.4, about 9.6, about 12.4, about 13.4, about 15.5, about 16.9, about 17.7, about 19.0, about 19.5, about 20.6, and about 22.5 degrees. In some embodiments, Form XV has an XRPD pattern substantially as shown in FIG. 21. In some embodiments, Form XV has a DSC thermogram characterized by an endothermic peak at a temperature of about 85° C., an endothermic peak at a temperature of about 172° C., an exothermic peak at a temperature of about 192° C., an endothermic peak at a temperature of about 268° C., or a combination thereof.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form. The term "hydrated," as used herein, is meant to refer to a crystalline form that includes water molecules in the crystalline lattice. Example "hydrated" crystalline forms include hemihydrates, monohydrates, dihydrates, and the like. Other hydrated forms such as channel hydrates and the like are also included within the meaning of the term.

The different crystalline forms of the compound provide herein (e.g., Compound 1) are characterized by X-ray powder diffraction (XRPD), differential scanning calorimetry (DSC), and/or thermogravimetric analysis (TGA). An X-ray powder diffraction (XRPD) pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear depending on the type of instrument or the settings (for example, whether a Ni filter is used or not). As used herein, the term "peak" or "characteristic peak" refers to a reflection having a relative height/intensity of at least about 3% of the maximum peak height/intensity. Moreover, instrument variation and other factors can affect the 2-theta values. Thus, peak assignments, such as those reported herein, can vary by plus or minus about 0.2° (2-theta), and the term "substantially" or "about" as used in the context of XRPD herein is meant to refer to the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound 1, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

In some embodiments, the compounds (or hydrates and solvates thereof) of the application are prepared in batches referred to as batches, samples, or preparations. The batches, samples, or preparations can include the compounds provided herein in any of the crystalline or non-crystalline forms described herein, including hydrated and non-hydrated forms, and mixtures thereof.

The compounds disclosed herein can include all isotopes of atoms occurring within them. Isotopes include those atoms having the same atomic number but different mass numbers. For example, isotopes of hydrogen include tritium and deuterium.

In some embodiments, the compounds provided herein (e.g., Compound 1), or salts thereof, or crystalline forms thereof, are substantially isolated. The term "substantially isolated" is meant that the compound or salt is at least partially or substantially separated from the environment in which it was formed or detected. Partial separation can include, e.g., a composition enriched in the compound, salts, or crystalline forms provided herein. Substantial separation can include compositions containing at least about 50%, at least about 60%, at least about 70%, at least about 80%, at least about 90%, at least about 95%, at least about 97%, or at least about 99% by weight of the compounds, salts, or crystalline forms provided herein.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Processes for Preparation of Compound 1

The present application further provides a process of preparing Compound 1, where the process can be suitable for scale up. A process of preparing Compound 1 is described in US 2015/0307493, the entirety of which is incorporated herein by reference. In comparison to the process described in US 2015/0307493, the process provided herein has certain advantages making it suitable for scale up. For example, process provided herein uses less hazardous reagents while affording high yields and good quality products. Further, the process provided herein can generate Compound 7 (see below) in situ without isolating of Compound 7, which provides better efficiency on a large scale.

In some embodiments, the process of preparing Compound 1 comprises reacting Compound 8:

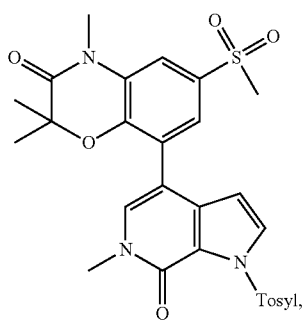

Compound 8 with B1, wherein B1 is a base.

In some embodiments, B1 is an alkali metal hydroxide base such as sodium hydroxide. The reacting of Compound 8 with B1 can be carried out in a solvent. In some embodiments, the solvent comprises an ether solvent such as 1,4-dioxane. Ether solvents such as 1,4-dioxane can afford Compound 1 in high yields and good quality. In some embodiments, the reacting of Compound 8 with B1 is carried out at elevated temperature, for example, at a temperature of about 50° C. to about 85° C. (e.g., about 60° C. to about 80° C. or about 65° C. to about 75° C.). In some embodiments, the temperature is about 70° C. In some embodiments, B1 is provided in molar excess with respect to the amount of Compound 8. In some embodiments, about 3 to about 4 or about 3.5 equivalent of B1 is used based on 1 equivalent of Compound 8.

In some embodiments, the process further comprises reacting Compound 7:

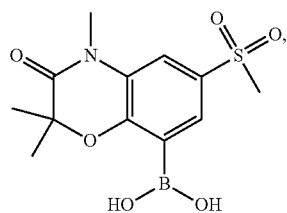

Compound 7 with Compound 9:

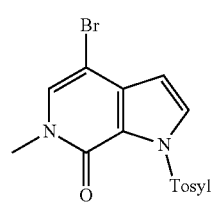

Compound 9 in the presence of P2 and B2 to form Compound 8, wherein P2 is a transition metal catalyst and B2 is a base.

In some embodiments, P2 is transition metal catalyst such as a palladium catalyst. Examples of palladium catalysts include [1,1'-bis(diphenylphosphino)ferrocene]dichloropalladium(II) (Pd(dppf)Cl$_2$, e.g., Pd(dppf)Cl$_2$—CH$_2$Cl$_2$), dichloro(bis{di-tert-butyl[4-(dimethylamino)phenyl]-phosphoranyl}Vanadium (Pd-132), Pd(PPh$_3$)$_4$, and tetrakis(tri(o-tolyl)phosphine)palladium(0). In some embodiments, P2 is Pd(dppf)Cl$_2$. In some embodiments, B2 is an alkali metal bicarbonate base such as sodium bicarbonate. In some embodiments, B2 is an alkali metal carbonate base such as K$_2$CO$_3$. The reacting of Compound 7 with Compound 9 can be carried out in a solvent. In some embodiments, the solvent comprises a protic solvent, an ether solvent, or a mixture thereof. In some embodiments, the solvent comprises water, 1,4-dioxane, or a mixture thereof. In some embodiments, the reacting of Compound 7 with Compound 9 is carried out at elevated temperature, for example, at a temperature of about 80° C. to about 100° C. (e.g., about 85° C. to about 95° C.). In some embodiments, the temperature is about 90° C. In some embodiments, about 1 equivalent of the Compound 9 is used based on 1 equivalent of Compound 7 or Compound 6 (which has the structure shown below). In some embodiments, P2 is provided in a sufficiently catalytic amount. For example, about 0.01 to about 0.05 or about 0.03 equivalent of P2 is used based on 1 equivalent of Compound 7. In some embodiments, B2 is provided in molar excess with respect to the amount of Compound 9. In some embodiments, about 2 to about 3 or about 2.5 equivalents of B2 is used based on 1 equivalent of Compound 9.

In some embodiments, the process further comprises reacting Compound 6:

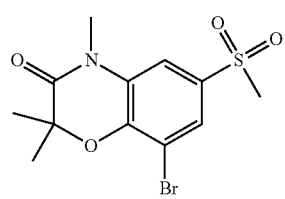

Compound 6 with 4,4,4',4',5,5,5',5'-octamethyl-2,2'-bi(1,3,2-dioxaborolane) in the presence of P3 and B3 to form Compound 7, wherein P3 is a transition metal catalyst and B3 is a base.

In some embodiments, P3 is a transition metal catalyst such as a palladium catalyst. Examples of palladium catalysts include [1,1'-bis(diphenylphosphino)ferrocene]dichloropalladium(II) (Pd(dppf)Cl$_2$, e.g., Pd(dppf)Cl$_2$—CH$_2$Cl$_2$), dichloro(bis{di-tert-butyl[4-(dimethylamino)phenyl]-phosphoranyl})palladium (Pd-132), Pd(PPh$_3$)$_4$, and tetrakis(tri(o-tolyl)phosphine)palladium(0). In some embodiments, P3 is Pd(dppf)Cl$_2$. In some embodiments, B3 is an alkali metal acetate base such as potassium acetate. The reacting of Compound 6 with 4,4,4',4',5,5,5',5'-octamethyl-2,2'-bi(1,3,2-dioxaborolane) can be carried out in a solvent. In some embodiments, the solvent comprises an ether solvent such as 1,4-dioxane. In some embodiments, the reacting of Compound 6 with 4,4,4',4',5,5,5',5'-octamethyl-2,2'-bi(1,3,2-dioxaborolane) is carried out at elevated temperature, for example, at a temperature of about 70° C. to about 90° C. (e.g., 75° C. to about 85° C.). In some embodiments, the temperature is about 80° C. In some embodiments, the reagent 4,4,4',4',5,5,5',5'-octamethyl-2,2'-bi(1,3,2-dioxaborolane) is provided in molar excess with respect to the amount of Compound 6. In some embodiments, about 2 to about 2.5 equivalents of 4,4,4',4',5,5,5',5'-octamethyl-2,2'-bi(1,3,2-dioxaborolane) is used based on 1 equivalent of Compound 6. In some embodiments, B3 is provided in molar excess with respect to the amount of Compound 6. In some embodiments, about 3 to about 3.5 equivalents of B3 is used based on 1 equivalent of Compound 6. In some embodiments, P3 is provided in a sufficiently catalytic amount. In some embodiments, about 0.01 to about 0.05 or about 0.03 equivalent of P3 is used based on 1 equivalent of Compound 6.

In some embodiments, the reacting to form Compound 7 and then subsequently to form Compound 8 is conducted in the same reaction vessel without the isolation of Compound 7. When the reacting to form Compound 7 and then Compound 8 is conducted in the same reaction vessel (without the isolation of Compound 7), Compound 8 can be formed from Compounds 7 and 9 without the addition of P2, e.g., by using P3 (a transition metal catalyst) in the same reaction vessel to form Compound 7. Alternatively, the coupling reactions to generate Compound 8 from Compound 6 can be carried out in two separate steps, where Compound 7 is isolated and P2 is employed in the reaction to generate Compound 8 from Compound 7.

Alternatively, Compound 8 can be prepared by a process comprising reacting Compound 6 with Compound 15:

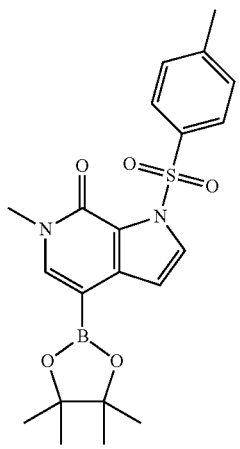

Compound 15 in the presence of P4 and B4, wherein P4 is transition metal catalyst and B4 is a base.

In some embodiments, P4 is a transition metal catalyst such as a palladium catalyst. Examples of palladium catalysts include 4-(di-tert-butylphosphino)-N,N-dimethylaniline-dichloropalladium (2:1), Pd(dppf)Cl$_2$ (e.g., Pd(dppf)Cl$_2$—CH$_2$Cl$_2$), dichloro(bis{di-tert-butyl[4-(dimethylamino)phenyl]-phosphoranyl})palladium (Pd-132), Pd(PPh$_3$)$_4$, and tetrakis(tri-o-tolyl)phosphine) palladium(0). In some embodiments, P4 is 4-(di-tert-butylphosphino)-N,N-dimethylaniline-dichloropalladium (2:1). In some embodiments, P4 is Pd(dppf)Cl$_2$ (e.g., Pd(dppf)Cl$_2$—CH$_2$Cl$_2$). In some embodiments, B4 is a base such as cesium fluoride. In another embodiment, B4 is an alkali metal carbonate such as K$_2$CO$_3$. The reacting of Compound 6 with Compound 15 can be carried out in a solvent. In some embodiments, the solvent comprises a protic solvent, an ether solvent, or a mixture thereof. In some embodiments, the reacting is carried out in a solvent comprising 1,4-dioxane, water, or a mixture thereof. In some embodiments, the reacting of Compound 6 with Compound 15 is carried out at an elevated temperature (e.g., higher than room temperature) such as at about reflux temperature. In some embodiments, about 1 equivalent of Compound 15 is used based on 1 equivalent of Compound 6. In some embodiments, B4 is provided in molar excess with respect to Compound 6. In some embodiments, about 3 to about 4 or about 3.5 equivalents of B4 is used based on 1 equivalent of Compound 6. P4 is typically provided in a sufficiently catalytic amount. In some embodiments, about 0.01 to about 0.1 or about 0.05 equivalent of P4 is used based on 1 equivalent of Compound 6.

In some embodiments, Compound 15 can be prepared by a process comprising reacting Compound 9 with 4,4,4',4',5,5,5',5'-octamethyl-2,2'-bi(1,3,2-dioxaborolane) in the presence of P8 and B8, wherein P8 is a transition metal catalyst and B8 is a base.

In some embodiments, P8 is a transition metal catalyst such as a palladium catalyst. Examples of palladium catalysts include tris(dibenzylideneacetone)dipalladium(0) (Pd$_2$(dba)$_3$, (di-tert-butylphosphino)-N,N-dimethylaniline-dichloropalladium (2:1), Pd(dppf)Cl$_2$ (e.g., Pd(dppf)Cl$_2$—CH$_2$Cl$_2$), dichloro(bis{di-tert-butyl[4-(dimethylamino)phenyl]-phosphoranyl})palladium (Pd-132), Pd(PPh$_3$)$_4$, and tetrakis(tri-o-tolyl)phosphine)palladium(0). In some embodiments, P8 is tris(dibenzylideneacetone)dipalladium (0) (Pd$_2$(dba)$_3$ (e.g., where dicyclohexyl(2',4',6'-triisopropylbiphenyl-2-yl)phosphine (Xphos) can be added as a ligand). In some embodiments, B8 is an alkali metal acetate base such as potassium acetate. The reacting of Compound 9 with 4,4,4',4',5,5,5',5'-octamethyl-2,2'-bi(1,3,2-dioxaborolane) can be carried out in a solvent. In some embodiments, the solvent comprises an ether solvent such as 1,4-dioxane. In some embodiments, the reacting of Compound 9 with 4,4,4',4',5,5,5',5'-octamethyl-2,2'-bi(1,3,2-dioxaborolane) is carried out at a temperature of about 75° C. to about 95° C. In some embodiments, the temperature is about 80° C. to about 90° C. or about 80° C. to about 85° C. In some embodiments, about 2 equivalent of 4,4,4',4',5,5,5',5'-octamethyl-2,2'-bi(1,3,2-dioxaborolane) is used based on 1 equivalent of Compound 9. In some embodiments, B8 is provided in molar excess with respect to Compound 9. In some embodiments, about 2 to about 3 of B8 is used based on 1 equivalent of Compound 9. P8 is typically provided in a sufficiently catalytic amount. In some embodiments, about 0.01 to about 0.1 or about 0.025 equivalent of P8 is used based on 1 equivalent of Compound 9.

In some embodiments, Compound 6 can be prepared according to the procedures in US2015/0307493, which is incorporated herein by reference in its entirety.

In some embodiments, Compound 6 is prepared by a process comprising reacting Compound 5:

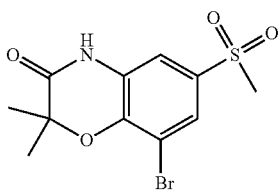

Compound 5 with a methylating agent and B5, wherein B5 is a base. In some embodiments, the methylating agent is methyl iodide (MeI), dimethyl sulfate, dimethyl carbonate, or tetramethylammonium chloride. In some embodiments, the methylating agent is methyl iodide. In some embodiments, B5 is an alkali metal carbonate base such as potassium carbonate ($K_2CO_3$). In some embodiments, the reacting of Compound 5 with the methylating agent is carried out in a solvent comprising, for example, an aprotic solvent such as N'N-dimethylformamide (DMF). In some embodiments, the reacting of Compound 5 with the methylating agent is carried out at a temperature of about 10° C. to about 20° C. or about 15° C. to about 20° C.

In some embodiments, Compound 5 is prepared by a process comprising reacting Compound 4:

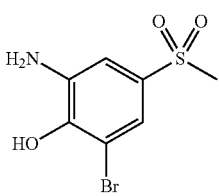

Compound 4 with 2-bromo-2-methylpropanoyl bromide and B6, wherein B6 is a base. In some embodiments, B6 is an alkali metal carbonate such potassium carbonate ($K_2CO_3$). The reacting of Compound 4 with 2-bromo-2-methylpropanoyl bromide can be conducted in the presence of a solvent. For example, the solvent comprises acetonitrile, water, or a mixture thereof. The reacting of Compound 4 with 2-bromo-2-methylpropanoyl bromide can be carried out at elevated temperature, for example, at a temperature of about 60° C. to about 90° C. In some embodiments, the temperature is about 75° C.

In some embodiments, Compound 4 is prepared by a process comprising reacting Compound 3:

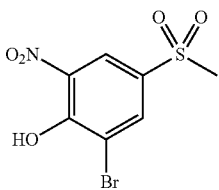

Compound 3 with a reducing agent. In some embodiments, the reducing agent is sodium hydrosulfite or $H_2$/Raney Ni. The reacting of Compound 3 with the reducing agent can be conducted in the presence of a solvent. In some embodiments, the solvent comprises a protic solvent (e.g., water and methanol), an ether solvent (tetrahydrofuran), or a mixture thereof. In some embodiments, the reacting of Compound 3 and sodium hydrosulfite is carried out in water, tetrahydrofuran, or a mixture thereof. In some embodiments, the reacting of Compound 3 with Hz/Raney Ni is carried out in methanol. In some embodiments, the reacting of Compound 3 with the reducing agent is carried out at room temperature. In some embodiments, sodium hydrosulfite is used in combination with sodium bicarbonate. The reacting of Compound 3 with sodium hydrosulfite and sodium bicarbonate can produce Compound 4 under mild process conditions as compared to Hz/Raney Ni, which can be hazardous on a large scale.

In some embodiments, Compound 3 is prepared by a process comprising reacting Compound 2:

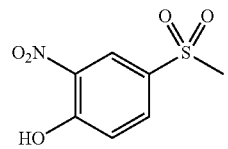

Compound 2 with N-bromosuccinimide (NBS). The use of NBS can provide high yields and good quality product on a large scale, e.g., on a kilo gram scale. In some embodiments, the reacting is carried out in a solvent comprising an aprotic solvent such as N,N-dimethylformamide (DMF). In some embodiments, the reacting is carried out at room temperature.

In some embodiments, Compound 2 is prepared by a process comprising reacting Compound 1a:

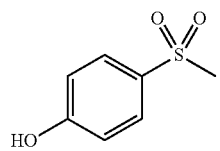

Compound 1a with nitric acid and acetic acid. In some embodiments, the reacting is carried out at a temperature of about 60° C. to about 90° C. or about 75° C. to about 80° C.

In some embodiments, Compound 9 can be prepared according to the procedures in US2015/0307493 and WO2013/097601, each of which is incorporated herein by reference in its entirety.

In some embodiments, Compound 9 is prepared by a process comprising reacting Compound 14:

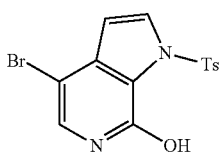

Compound 14 with methyl iodide and sodium hydride. In some embodiments, the reacting is carried out in a solvent comprising an aprotic solvent such as N'N-dimethylformamide (DMF).

In some embodiments, Compound 14 is prepared by a process comprising reacting Compound 13:

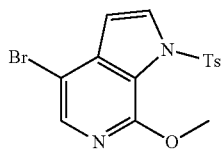

Compound 13 with an acid. In some embodiments, the acid is a strong aqueous acid such as HCl. In some embodiments, the reacting is carried out in a solvent comprising an ether solvent such as 1,4-dixoane.

In some embodiments, Compound 13 is prepared by a process comprising reacting Compound 12:

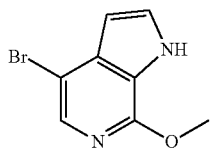

Compound 12 with p-toluenesulfonyl chloride (p-TsCl) and sodium hydride (NaH). In some embodiments, the reacting is carried out in a solvent comprising an aprotic solvent such as N'N-dimethylformamide (DMF).

In some embodiments, Compound 12 is prepared by a process comprising reacting Compound 11:

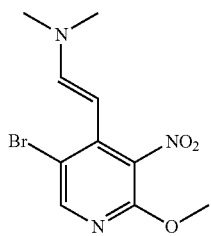

Compound 11 with iron (Fe) and acetic acid (HOAc). In some embodiments, the reacting is carried out in a solvent comprising an ether solvent such as tetrahydrofuran (THF). The combination of iron and acetic acid can be employed as a reducing agent and can be a safer alternative to reducing agent such as $H_2$/Raney Ni, which can be hazardous on a large scale.

In some embodiments, Compound 11 is prepared by a process comprising reacting Compound 10:

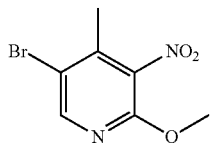

Compound 10 with 1,1-diethoxy-N,N-dimethylmethanamine with B7, wherein B7 is a base. In some embodiments, B7 is an alkali metal alkoxide such lithium methanolate. In some embodiments, the reacting is carried out in a solvent comprising an aprotic solvent such as N'N-dimethylformamide (DMF).

In some embodiments, the process of preparing Compound 6 comprises:
(i) reacting Compound 1a with nitric acid and acetic acid to form Compound 2;
(ii) reacting Compound 2 with N-bromosuccinimide (NBS) to form Compound 3;
(iii) reacting Compound 3 with a reducing agent to form Compound 4;
(iv) reacting Compound 4 with 2-bromo-2-methylpropanoyl bromide and B6 to form Compound 5; and
(v) reacting Compound 5 with a methylating agent and B5 to form Compound 6.

In some embodiments, the process of preparing Compound 9 comprises:
(i) reacting Compound 10 with 1,1-diethoxy-N,N-dimethylmethanamine with B7 to form Compound 11;
(ii) reacting Compound 11 with iron (Fe) and acetic acid (HOAc) to form Compound 12;
(iii) reacting Compound 12 with p-toluenesulfonyl chloride (p-TsCl) and sodium hydride (NaH) to form Compound 13;
(iv) reacting Compound 13 with an acid to form Compound 14; and
(v) reacting Compound 14 with methyl iodide and sodium hydride to form Compound 9.

In some embodiments, the process of preparing Compound 1, or a salt thereof, comprises:
(i) reacting Compound 6 with 4,4,4',4',5,5,5',5'-octamethyl-2,2'-bi(1,3,2-dioxaborolane) in the presence of P3 and B3 to form Compound 7;
(ii) reacting Compound 7 with Compound 9 in the presence of P2 and B2 to form Compound 8; and
(iii) reacting Compound 8 with B1 to form Compound 1, or a salt thereof.

In some embodiments, the process of preparing Compound 1, or a salt thereof, comprises:
(i) reacting Compound 6 with Compound 15 in the presence of P4 and B4 to form Compound 8; and
(ii) reacting Compound 8 with B1 to form Compound 1, or a salt thereof.

In some embodiments, the process of preparing Compound 1, or a salt thereof, comprises:
(i) reacting Compound 9 with 4,4,4',4',5,5,5',5'-octamethyl-2,2'-bi(1,3,2-dioxaborolane) in the presence of P8 and B8 to form Compound 15;
(ii) reacting Compound 6 with Compound 15 in the presence of P4 and B4 to form Compound 8; and
(iii) reacting Compound 8 with B1 to form Compound 1, or a salt thereof.

In some embodiments, the process of preparing Compound 1 comprises:
(i) reacting Compound 1a with nitric acid and acetic acid to form Compound 2;
(ii) reacting Compound 2 with N-bromosuccinimide (NBS) to form Compound 3;
(iii) reacting Compound 3 with a reducing agent to form Compound 4;
(iv) reacting Compound 4 with 2-bromo-2-methylpropanoyl bromide and B6 to form Compound 5;
(v) reacting Compound 5 with a methylating agent and B5 to form Compound 6;
(vi) reacting Compound 6 with 4,4,4',4',5,5,5',5'-octamethyl-2,2'-bi(1,3,2-dioxaborolane) in the presence of P3 and B3 to form Compound 7; (vii) reacting Compound 7 with Compound 9 in the presence of P2 and B2 to form Compound 8; and (viii) reacting Compound 8 with B1 to form Compound 1.

In some embodiments, the process of preparing Compound 1 comprises:

(i) reacting Compound 1a with nitric acid and acetic acid to form Compound 2;

(ii) reacting Compound 2 with N-bromosuccinimide (NBS) to form Compound 3;

(iii) reacting Compound 3 with a reducing agent to form Compound 4;

(iv) reacting Compound 4 with 2-bromo-2-methylpropanoyl bromide and B6 to form Compound 5;

(v) reacting Compound 5 with a methylating agent and B5 to form Compound 6;

(vi) reacting Compound 6 with Compound 15 in the presence of P4 and B4 to form Compound 8; and (vii) reacting Compound 8 with B1 to form Compound 1.

In some embodiments, the process of preparing Compound 1 comprises:

(i) reacting Compound 10 with 1,1-diethoxy-N,N-dimethylmethanamine with B7 to form Compound 11;

(ii) reacting Compound 11 with iron (Fe) and acetic acid (HOAc) to form Compound 12;

(iii) reacting Compound 12 with p-toluenesulfonyl chloride (p-TsCl) and sodium hydride (NaH) to form Compound 13;

(iv) reacting Compound 13 with an acid to form Compound 14;

(v) reacting Compound 14 with methyl iodide and sodium hydride to form Compound 9;

(vi) reacting Compound 7 with Compound 9 in the presence of P2 and B2 to form Compound 8; and (vii) reacting Compound 8 with B1 to form Compound 1.

In some embodiments, the process of preparing Compound 1 comprises:

(i) reacting Compound 10 with 1,1-diethoxy-N,N-dimethylmethanamine with B7 to form Compound 11;

(ii) reacting Compound 11 with iron (Fe) and acetic acid (HOAc) to form Compound 12;

(iii) reacting Compound 12 with p-toluenesulfonyl chloride (p-TsCl) and sodium hydride (NaH) to form Compound 13;

(iv) reacting Compound 13 with an acid to form Compound 14;

(v) reacting Compound 14 with methyl iodide and sodium hydride to form Compound 9;

(vi) reacting Compound 9 with 4,4,4',4',5,5,5',5'-octamethyl-2,2'-bi(1,3,2-dioxaborolane) in the presence of P8 and B8 to form Compound 15;

(vii) reacting Compound 6 with Compound 15 in the presence of P4 and B4 to form Compound 8; and (viii) reacting Compound 8 with B1 to form Compound 1.

In some embodiments, provided herein is a compound which is

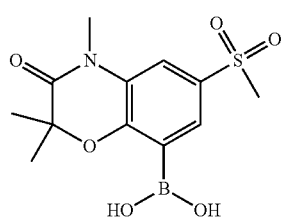

Compound 7 or a salt thereof.

In some embodiments, provided herein is a process of reacting Compound 6 with 4,4,4',4',5,5,5',5'-octamethyl-2,2'-bi(1,3,2-dioxaborolane) in the presence of P3 and B3 to form Compound 7.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

In some embodiments, a solution of Compound 1 at elevated temperature as described herein refers to a solution at a temperature that is above room temperature. For example, solution of Compound 1 at elevated temperature would have a temperature above about room temperature, e.g., above about 20° C., above about 30° C., above about 40° C., above about 50° C., above about 60° C., above about 70° C., above about 80° C., above about 90° C., or above about 100° C.

In some embodiments, concentrating a solution as described herein refers to a solution where its volume is reduced by letting the solvent evaporate, by heating the solution, by subjecting the solution to reduced pressure, or any combination thereof.

As used herein, the phrase "alkali metal bicarbonate base," employed alone or in combination with other terms, refers to a base having formula $M(HCO_3)$, wherein M refers to an alkali metal (e.g. lithium, sodium, or potassium). Example alkali metal bicarbonate bases include, but are not limited to, lithium bicarbonate, sodium bicarbonate, and potassium bicarbonate.

As used herein, the phrase "alkali metal carbonate base," employed alone or in combination with other terms, refers to a base having formula $M_2CO_3$, wherein M refers to an alkali metal (e.g. lithium, sodium, or potassium). Example alkali metal carbonate bases include, but are not limited to lithium carbonate, sodium carbonate, and potassium carbonate.

As used herein, the phrase "alkali metal hydroxide base," employed alone or in combination with other terms, refers to a base having formula MOH, wherein M refers to an alkali metal (e.g. lithium, sodium, or potassium). Example alkali metal hydroxide bases include, but are not limited to lithium hydroxide, sodium hydroxide, and potassium hydroxide.

As used herein, the phrase "alkali metal acetate base," employed alone or in combination with other terms, refers to a base having formula $M(OC(O)CH_3)$, wherein M refers to an alkali metal (e.g. lithium, sodium, or potassium). Example alkali metal acetate bases include, but are not limited to lithium acetate, sodium acetate, and potassium acetate.

As used herein, the phrase "transition metal catalyst" refers to a metal catalyst (e.g., palladium or nickel catalyst) suitable to catalyze a carbon-carbon coupling reaction. Example transition metal catalysts include, but are not limited to, $PdCl_2(PPh_3)_2$, $Pd(PPh_3)_4$, dichloro(bis{di-tert-butyl[4-(dimethylamino)phenyl]-phosphoranyl})palladium (Pd-132), $NiCl_2(dppf)$, and $NiCl_2(dppp)$, where (dppf) refers to 1,1'-bis(diphenylphosphino)ferrocene and (dppp) refers to 1,3-bis(diphenylphosphino)propane.

Example palladium catalysts include but are not limited to $PdCl_2(PPh_3)_2$, $Pd(PPh_3)_4$, dichloro(bis{di-tert-butyl[4-(dimethylamino)phenyl]-phosphoranyl}Vanadium (Pd-132), palladium on carbon, $PdCl_2$, $Pd(OAc)_2$, $PdCl_2(MeCN)_2$, tris(dibenzylideneacetone)dipalladium(0) $(Pd_2(dba)_3$, 4-(ditert-butylphosphino)-N,N-dimethylaniline-dichloropalladium (2:1), Pd(dppf)Cl$_2$ (e.g., Pd(dppf)Cl$_2$—CH$_2$Cl$_2$), and tetrakis(tri(o-tolyl)phosphine)palladium(0).

As used herein, the term "reacting," is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

In some embodiments, anti-solvent as described herein refers to a solvent where Compound 1 is less soluble relative to another solvent or solvent mixture in the solution. For example, anti-solvent can include but not limited to benzene, cyclohexane, pentane, hexane, heptane (e.g., n-heptane), toluene, cycloheptane, methylcyclohexane, heptane, ethylbenzene, m-, o-, or p-xylene, octane, indane, nonane, or naphthalene.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

Methods of Use

Compound 1, or a salt thereof, is a BET protein inhibitor and thus, is useful in treating diseases and disorders associated with activity of BET proteins. For the uses described herein, any forms of Compound 1, including any of the embodiments described herein, may be used.

Compound 1 can inhibit one or more of BET proteins BRD2, BRD3, BRD4, and BRD-t. In some embodiments, Compound 1 selectively inhibits one or more BET proteins over another. "Selective" means that the compound binds to or inhibits a BET protein with greater affinity or potency, respectively, compared to a reference, such as another BET protein. For example, the compound can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compound inhibits two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

Compound 1 is therefore useful for treating BET protein mediated disorders. The term "BET protein mediated disorder" or "BET-mediated disorder" refers to any disorder, disease or condition in which one or more of the BET proteins, such as BRD2, BRD3, BRD4 and/or BRD-t, or a mutant thereof, plays a role, or where the disease or condition is associated with expression or activity of one or more of the BET proteins. Compound 1, as an inhibitor of BET proteins, can therefore be used to treat or lessen the severity of diseases and conditions where BET proteins, such as BRD2, BRD3, BRD4, and/or BRD-t, or a mutant thereof, are known to play a role.

Diseases and conditions treatable using Compound 1 include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of Compound 1, or any of the embodiments thereof, or a pharmaceutical composition thereof. The present disclosure also provides a solid form of Compound 1, or any of the embodiments thereof, or a pharmaceutical composition comprising the solid form, for use in treating a BET-mediated disease or disorder. Also provided is the use of a solid form of Compound 1, or any of the embodiments thereof, or a pharmaceutical composition comprising the solid form, in the manufacture of a medicament for treating a BET-mediated disease or disorder.

Diseases that can be treated with Compound 1 include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, acute myeloid leukemia (AML), diffuse large B-cell lymphoma (DLBCL), ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

In some embodiments, the cancer is a hematological cancer.

In some embodiments, the cancer is multiple myeloma, acute myeloid leukemia (AML), or diffuse large B-cell lymphoma (DLBCL).

The diseases treatable using Compound 1 also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with Compound 1 also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with Compound 1 also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleraciema, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with Compound 1 also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with Compound 1 include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. Compound 1 can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In some embodiments, Compound 1 can be used in the treatment of human papilloma virus infections of skin or cervical epithelia.

The diseases and conditions that can be treated with Compound 1 also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastrointestinal or peripheral limb embolism.

Compound 1 is also useful in the treatment of disorders of lipid metabolism via the regulation of APO-A1 such as hypercholesterolemia, atherosclerosis and Alzheimer's disease.

Compound 1 is also useful in the treatment of fibrotic conditions such as idiopathic pulmonary fibrosis, renal fibrosis, post-operative stricture, keloid formation, scleroderma and cardiac fibrosis.

Compound 1 can also be used to treat ophthamological indications such as dry eye.

Compound 1 can also be used to treat heart disease such as heart failure.

As used herein, the term "contacting" refers to the bringing together of indicated moieties in an in vitro system or an in vivo system. For example, "contacting" a BET protein with Compound 1 (e.g., a solid form of Compound 1 such as a crystalline solid form) includes the administration of Compound 1 to an individual or patient, such as a human, having a BET protein, as well as, for example, introducing solid form of a compound provided herein into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

Compound 1 can be used in combination treatments where Compound 1 is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, Compound 1 can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, Compound 1 can be used in combination with chemotherapeutic agents, or other anti-proliferative agents. Compound 1 can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, Compound 1 can be used in combination with ruxolitinib.

Compound 1 can be used in combination with one or more immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

Compound 1 can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, Compound 1 can be administered in combination with a corticosteroid such as triamcinolone, dexamethasone, fluocinolone, cortisone, prednisolone, or flumetholone.

For treating autoimmune or inflammatory conditions, Compound 1 can be administered in combination with an immune suppressant such as fluocinolone acetonide (Retisert®), rimexolone (AL-2178, Vexol, Alcon), or cyclosporine (Restasis®).

For treating autoimmune or inflammatory conditions, Compound 1 can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3, 4-dihydroxy-5-[6-[(3-iodophenyl)methylamino]purin-9- yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, Compound 1 can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

In some embodiments, Compound 1 is administered in combination with a JAK kinase inhibitor (e.g., ruxolitinib, tofacitinib, baricitinib, CYT387, GLPG0634, lestaurtinib, pacritinib, TG101348, or a JAK1-selective inhibitor), a Pim kinase inhibitor (including inhibitors of one or more of PIM1, PIM2, and PIM3), a PI3 kinase inhibitor including PI3K-delta selective and broad spectrum PI3K inhibitors, an MEK inhibitor, a cyclin dependent kinase inhibitor, a b-RAF inhibitor, an mTOR inhibitor, a proteasome inhibitor (e.g., bortezomib, carfilzomib), an HDAC-inhibitor (e.g., panobinostat, vorinostat), a DNA methyl transferase inhibitor, dexamethasone, melphalan, or an immunomodulator (e.g., lenolidomide, pomalidomide).

Formulation, Dosage Forms and Administration

When employed as pharmaceuticals, Compound 1 (e.g., a solid form of Compound 1 such as a crystalline solid form) can be administered as pharmaceutical compositions. These compositions can be prepared in a manner well known in the pharmaceutical art, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This application also includes pharmaceutical compositions which contain, as the active ingredient, Compound 1 or a pharmaceutically acceptable salt thereof, in combination with one or more pharmaceutically acceptable carriers (excipients). In some embodiments, the composition is suitable for topical administration. In making the compositions of described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, Compound 1 can be milled to provide the appropriate particle size prior to combining with the other ingredients. If Compound 1 is substantially insoluble, it can be milled to a particle size of less than 200 mesh. If Compound 1 is substantially water soluble, the particle size can be adjusted by milling to provide a substantially uniform distribution in the formulation, e.g., about 40 mesh.

Compound 1 may be milled using known milling procedures such as wet milling to obtain a particle size appropriate for tablet formation and for other formulation types. Finely divided (nanoparticulate) preparations of Compound 1 can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

The compositions can be formulated in a unit dosage form containing a desired amount of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of provided herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above.

The tablets or pills described herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the Compound 1 and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage Compound 1 can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions provided herein can further include one or more additional pharmaceutical agents such as a chemotherapeutic, steroid, anti-inflammatory compound, or immunosuppressant, examples of which are listed hereinabove.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Example 1. Synthesis of 2,2,4-Trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one (Compound 1)

Synthesis of intermediate Compound 5 was carried out according to Scheme 1.

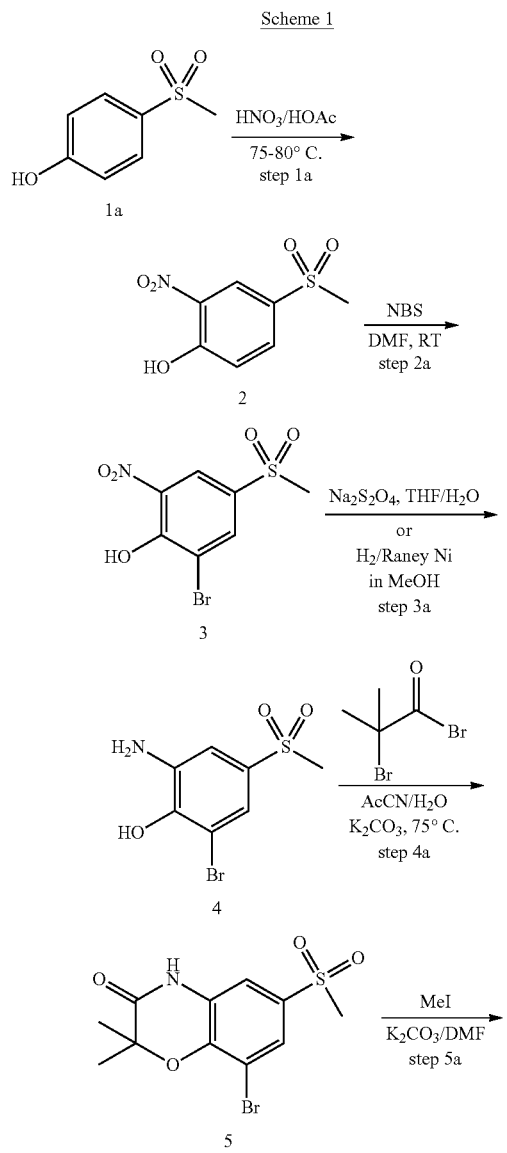

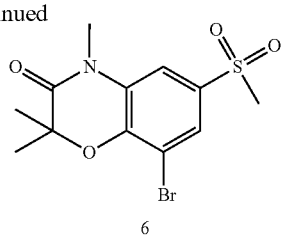

Step 1a. 4-(Methylsulfonyl)-2-nitrophenol (Compound 2)

Nitric acid (69%, 4.2 mL, 70 mmol, 1.2 equiv) was added over one minute to a stirred solution of 4-(methylsulfonyl)-phenol (Compound 1a, 10 g, 58.1 mmol) in acetic acid (HOAc, 91 mL) at room temperature. The reaction was heated to 70° C., when an exotherm was observed. The reaction mixture was stirred at 75-80° C. for three hours. Nitric acid (69%, 0.3 mL, 5.0 mmol, 0.086 equiv) was added and the mixture was stirred for an additional one hour. The reaction mixture was cooled to 15° C. and water (230 mL) was added. After stirring for 30 minutes, the resulting solids were collected by filtration, rinsed with water (2×45 mL), and dried under vacuum at 45° C. for 5 hours to give the crude desired product, 4-(methylsulfonyl)-2-nitrophenol (Compound 2, 11.0 g). The crude Compound 2 was then dissolved in tetrahydrofuran (THF, 110 mL) at 55° C. and warm water (45° C., 275 mL) was added slowly. The solution was gradually cooled to room temperature and stirred at room temperature overnight before being further cooled to 9° C. and stirred at 9° C. for one hour. The solids were collected by filtration and dried under vacuum at 50° C. overnight to give 4-(methylsulfonyl)-2-nitrophenol (Compound 2, 10.15 g, 12.6 g theoretical, 80.6% yield) as a yellow powder. Compound 2: LCMS calculated for $C_7H_8NO_4S$ $(M+H)^+$: 218.0, Found: 218.1; $^1H$ NMR (300 MHz, DMSO-$d_6$) δ 12.20 (br s, 1H), 8.34 (d, J=2.4 Hz, 1H), 8.00 (dd, J=8.8 Hz, J=2.4 Hz, 1H), 7.30 (d, J=8.8 Hz, 1H), 3.22 (s, 3H) ppm.

Step 2a. 2-Bromo-4-(methylsulfonyl)-6-nitrophenol (Compound 3)

N-Bromosuccinimide (NBS, 680 g, 3.82 moles, 1.0 equiv) was added at 0° C. to a solution of 4-(methylsulfonyl)-2-nitro-phenol (Compound 2, 825 g, 3.8 moles) in DMF (5.9 L). The cooling bath was removed after 10 minutes and the reaction mixture was stirred at room temperature for two hours. When LCMS indicated the reaction was complete, water (5.9 L) was added and the mixture was stirred at room temperature for one hour. The solids were filtered, washed with water (3×2.5 L) and dried under vacuum at 45° C. overnight to give 2-bromo-4-(methylsulfonyl)-6-nitrophenol (Compound 3, 1085 g, 1131.1 g theoretical, 95.9% yield) as yellow powder, which was used in the subsequent reaction without further purification. Compound 3: LCMS calculated for $C_7H_6BrNO_5S$ $(M-H)^-$: 293.9, Found: 294.0; $^1H$ NMR (300 MHz, DMSO-$d_6$) δ 8.33 (d, J=2.0 Hz, 1H), 8.31 (d, J=2.0 Hz, 1H), 3.27 (s, 3H) ppm.

Step 3a. 2-Amino-6-bromo-4-(methylsulfonyl)phenol (Compound 4)

Sodium bicarbonate ($NaHCO_3$, 2.6 kg, 30.95 moles, 8.8 equiv) was added portion wise over one hour to a solution of 2-bromo-4-(methylsulfonyl)-6-nitrophenol (Compound 3, 1037 g, 3.5 moles) and sodium hydrosulfite ($Na_2S_2O_4$, 85% technical grade, 3.15 kg, 15.4 moles, 4.4 equiv) in a 1 to 1 mixture of tetrahydrofuran (THF, 10 L) and water (10 L). The resulting reaction mixture was stirred at room temperature for two hours. When LCMS indicated the reaction was complete, the reaction mixture was extracted with ethyl acetate (EtOAc, 2×10 L). The combined organic layers were concentrated under reduced pressure. The residue was dissolved in ethyl acetate (EtOAc, 13 L) and the insoluble material was removed by filtration. The filtrate was evaporated under reduced pressure to afford crude 2-amino-6-bromo-4-(methylsulfonyl)phenol (Compound 4, 736.5 g, 931.4 g theoretical, 79% yield) as beige powder, which was used in the subsequent reaction without further purification. Compound 4: LCMS calculated for $C_7H_8BrNO_3S$ $(M+H)^+$: 265.9, Found: 266.1; $^1H$ NMR (300 MHz, DMSO-$d_6$) δ 7.15 (d, J=2.4 Hz, 1H), 7.10 (d, J=2.4 Hz, 1H), 6.8 (br s, 2H), 3.4 (br s, 1H), 3.09 (s, 3H) ppm.

Step 4a. 8-Bromo-2,2-dimethyl-6-(methylsulfonyl)-2H-benzo[b][1,4]oxazin-3(4H)-one (Compound 5)

A solution of potassium carbonate ($K_2CO_3$, 842 g, 6.1 moles, 4.15 equiv) in water (2.8 L) was added to a solution of 2-amino-6-bromo-4-(methylsulfonyl)phenol (Compound 4, 391 g, 1.47 moles) in acetonitrile (8 L) at room temperature. 2-Bromo-2-methylpropanoyl bromide (466 mL, 864 g, 3.76 moles, 2.56 equiv) was then added to the reaction mixture over 20 minutes at room temperature and the resulting reaction mixture was stirred at room temperature overnight. When LCMS indicated the corresponding ring-open intermediate had formed, the reaction mixture was heated to 75° C. for 6 hours. The reaction mixture was concentrated under reduced pressure to half volume. Water (4 L) and 1 N aqueous hydrochloric acid (HCl, 2.24 L) were added and the mixture was stirred for 15 minutes. The solids were collected by filtration, washed with water (1.2 L), and dried under vacuum at 50° C. overnight to give the crude desired product (Compound 5, 404 g). The crude product was then triturated with a 5 to 1 mixture of heptanes and MTBE (1.2 L) at room temperature for three hours. The solids were collected by filtration, washed with heptanes (1 L), and dried under vacuum to afford 8-bromo-2,2-dimethyl-6-(methylsulfonyl)-2H-benzo[b][1,4]oxazin-3(4H)-one (Compound 5, 401 g, 491.3 g theoretical, 81.6% yield, 98% purity) as yellow to brown powders. Compound 5: LCMS calculated for $C_{11}H_{12}BrNO_4S$ $(M+H)^+$: 334.0, Found: 333.9; $^1H$ NMR (300 MHz, DMSO-$d_6$) δ 11.10 (s, 1H), 7.74 (d, J=2.0 Hz, 1H), 7.38 (d, J=2.0 Hz, 1H), 3.22 (s, 3H), 1.46 (s, 6H) ppm.

Step 5a. 8-Bromo-2,2,4-trimethyl-6-(methylsulfonyl)-2H-benzo[b][1,4]oxazin-3(4H)-one (Compound 6)

A 200 L glass reactor was assembled with an overhead stirring, thermocouple, addition funnel, and a nitrogen inlet and the apparatus was purged with nitrogen. DMF (30.0 L) and 8-bromo-2,2-dimethyl-6-(methylsulfonyl)-2H-benzo[b][1,4]oxazin-3(4H)-one (Compound 5, 3000 g, 8.98 moles) were charged to the reactor and the mixture was stirred at ambient temperature until a solution was obtained. Potassium carbonate ($K_2CO_3$, 1371 g, 9.92 moles, 1.11 equiv) and methyl iodide (MeI, 1536 g, 0.67 L, 10.83 moles, 1.21 equiv) were then charged to the reactor while maintaining the internal temperature at about 17° C. The resulting reaction mixture was stirred for about 4 hours until the methylation reaction completion was indicated by HPLC. Potable water (60.0 L) was charged to the reactor while maintaining the internal temperature at about 19° C. and the mixture was stirred at ambient temperature for about 2.5 hours. The solids were collected by filtration and the wet cake was washed with potable water (30.0 L) and air-dried for about 15.5 hours followed by drying under vacuum at about 45° C. to afford crude 8-bromo-2,2,4-trimethyl-6-(methylsulfonyl)-2H-benzo[b][1,4]oxazin-3(4H)-one (Compound 6, 2834 g, 3127 g theoretical, 90.6% yield) as off-white to yellow powder, which was used in the subsequent reaction without further purification. Compound 6: $^1H$ NMR (400 MHz, DMSO-$d_6$) δ 7.83 (d, J=1.9 Hz, 1H), 7.59 (d, J=1.9 Hz, 1H), 3.37 (s, 3H), 3.31 (d, J=3.4 Hz, 3H), 1.49 (s, 6H) ppm; $^{13}C$ NMR (101 MHz, DMSO-$d_6$) δ 167.47 (s), 144.14 (s), 136.03 (s), 131.46 (s), 126.07 (s), 113.71 (s), 111.25 (s), 79.80 (s), 43.98 (s), 29.42 (s), 24.28 (s) ppm.

Synthesis of intermediate Compound 9 was carried out according to Scheme 2.

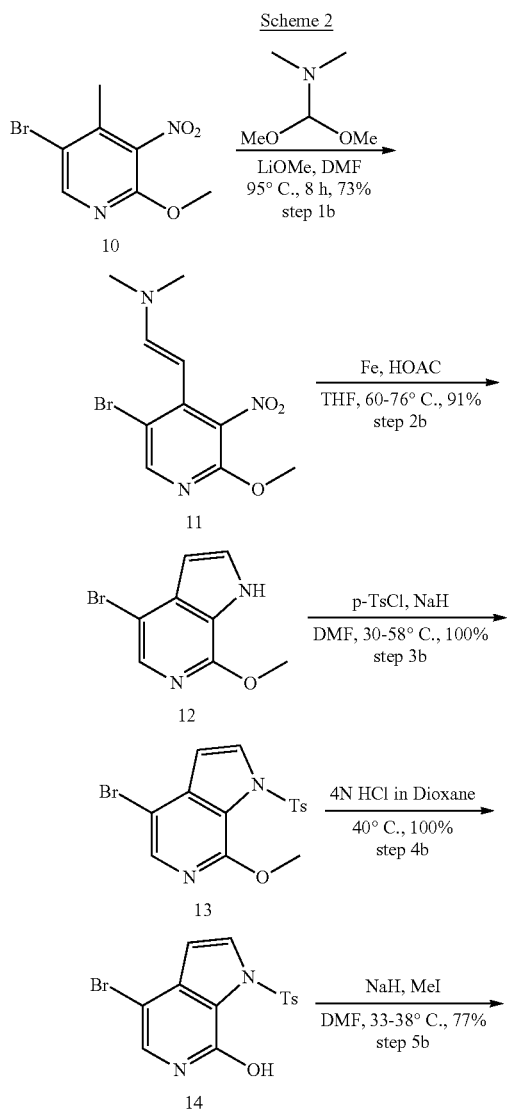

-continued

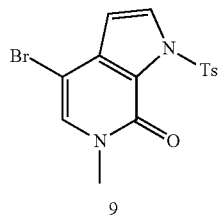

9

Step 1b. (E)-2-(5-Bromo-2-methoxy-3-nitropyridin-4-yl)-N,N-dimethylethenamine (Compound 11)

Lithium methanolate (11.5 g, 0.303 moles, 0.147 equiv) in methanol (300 mL) was added to a solution of 5-bromo-2-methoxy-4-methyl-3-nitropyridine (Compound 10, 508 g, 2.057 moles) in DMF (5.0 L). The reaction mixture was heated to 90° C. and 1,1-dimethoxy-N,N-dimethylmethanamine (2180 mL, 8.0 equiv) was added over 10 minutes. The reaction mixture was stirred at 90-95° C. overnight. When LCMS indicated the reaction was complete, the reaction mixture was cooled to 5° C. and ice-cold water (12.2 L) was added from an addition funnel. The mixture was stirred in cooling bath for one hour and the precipitated solids were collected by filtration. The solids were washed with ice cold water (2 L), suction dried for two hours, then dried under vacuum at 40° C. overnight to afford crude (E)-2-(5-bromo-2-methoxy-3-nitropyridin-4-yl)-N,N-dimethylethenamine (Compound 11, 506 g, 619.2 g theoretical, 81.7% yield) as red solid, which was used in the subsequent reaction without further purification. Compound 11: $^{1}$H NMR (300 MHz, DMSO-$d_6$) δ 8.22 (s, 1H), 7.03 (d, J=3.5 Hz, 1H), 4.79 (d, J=3.5 Hz, 1H), 3.86 (s, 3H), 2.89 (s, 6H) ppm.

Step 2b. 4-Bromo-7-methoxy-1H-pyrrolo[2,3-c]pyridine (Compound 12)

Iron powder (Fe, 1085 g, 19.5 moles, 10 equiv) and acetic acid (HOAc, 4380 mL, 4595 g, 76.5 moles, 39.3 equiv) were sequentially added to a solution of (E)-2-(5-bromo-2-methoxy-3-nitropyridin-4-yl)-N,N-dimethylethenamine (Compound 11, 587 g, 1.95 moles) in tetrahydrofuran (THF, 5.25 L). The reaction mixture was heated to 40° C., causing a slow and steady exothermic to 77° C. over one hour. After stirring at 75° C. for an additional two hours, LCMS indicated the reaction was complete. The reaction mixture was cooled to 50° C., diluted with ethyl acetate (EtOAc, 4 L) and stirred at room temperature overnight. The solids were removed by filtration through celite, which was rinsed with ethyl acetate (EtOAc, 6 L). The combined filtrates were concentrated under reduced pressure. The residue was dissolved in ethyl acetate (EtOAc, 16 L) and the solution was washed with a solution of sodium carbonate ($Na_2CO_3$, 900 g) in water (12 L) and with saturated brine (2 L). The combined aqueous layers were extracted with ethyl acetate (EtOAc, 4 L). The combined organic layers were evaporated under reduced pressure. Heptanes (4 L) were added and the solvents were removed under reduced pressure to afford crude 4-bromo-7-methoxy-1H-pyrrolo[2,3-c]pyridine (Compound 12, 450 g) quantitatively as dark solid, which was used in the subsequent reaction without further purification. Compound 12: LCMS calculated for $C_8H_7BrN_2O$ (M+H)$^+$: 227.0, Found: 227.1; $^{1}$H NMR (300 MHz, DMSO-$d_6$) δ 7.73 (s, 1H), 7.53 (d, J=3.0 Hz, 1H), 6.40 (d, J=3.0 Hz, 1H), 3.99 (s, 3H) ppm.

Step 3b. 4-Bromo-7-methoxy-1-tosyl-1H-pyrrolo[2,3-c]pyridine (Compound 13)

A 60% dispersion of sodium hydride in mineral oil (NaH, 120 g, 3 moles, 1.5 equiv) was added portion-wise over 15 minutes to a solution of crude 4-bromo-7-methoxy-1H-pyrrolo[2,3-c]pyridine (Compound 12, 450 g, 1.95 moles) in DMF (4.5 L). The temperature of the reaction mixture reached 38° C. The reaction mixture was stirred for 10 minutes before being cooled to 20° C. p-Toluenesulfonyl chloride (p-TsCl, 562 g, 2.95 moles, 1.5 equiv) was added all at once and the mixture was stirred at room temperature for two hours. When LCMS indicated the reaction was complete, water (9 L) was added. The solids were collected by filtration, rinsed with water (2.5 L), then dissolved in ethyl acetate (EtOAc, 5 L). The solution was washed with water (3 L). The aqueous layer was back extracted with ethyl acetate (EtOAc, 3 L). The combined organic layers were concentrated under reduced pressure to give crude 4-bromo-7-methoxy-1-tosyl-1H-pyrrolo[2,3-c]pyridine (Compound 13, 801 g) quantitatively as dark solid, which was used in the subsequent reaction without further purification. Compound 13: LCMS calculated for $C_{15}H_{13}BrN_2O_3S$ (M+H)$^+$: 381.0; Found: 381.0; $^{1}$H NMR (300 MHz, DMSO-$d_6$) δ 8.15 (d, J=3.8 Hz, 1H), 7.97 (s, 1H), 7.83 (d, J=8.5 Hz, 2H), 7.43 (d, J=8.5 Hz, 2H), 6.78 (d, J=3.8 Hz, 1H), 3.80 (s, 3H), 2.36 (s, 3H) ppm.

Step 4b. 4-Bromo-1-tosyl-1H-pyrrolo[2,3-d]pyridin-7-ol (Compound 14)

Crude 4-bromo-7-methoxy-1-tosyl-1H-pyrrolo[2,3-c]pyridine (Compound 13, 801 g, 1.95 moles) was dissolved in a solution of 4 M HCl in 1,4-dioxane (5.6 L, 22.4 moles, 11.5 equiv) and stirred at 40-45° C. for 12 hours. The reaction mixture was concentrated under reduced pressure and the residue was suspended in ethyl ether ($Et_2O$, 1.5 L). The solids were filtered and washed sequentially with ethyl ether ($Et_2O$, 0.5 L) and heptanes (1 L) before being dried under vacuum at 40° C. overnight to give crude 4-bromo-1-tosyl-1H-pyrrolo[2,3-c]pyridin-7-ol (Compound 14, 648 g, 716 g theoretical, 90.5% yield over three steps) as yellow powder, which was used in the subsequent reaction without further purification. Compound 14: LCMS calculated for $C_{14}H_{11}BrN_2O_3S$ (M+H)$^+$: 367.0, Found: 366.9; $^{1}$H NMR (300 MHz, DMSO-$d_6$) δ 11.46 (s, 1H), 8.01 (d, J=3.5 Hz, 1H), 7.92 (d, J=8.2 Hz, 2H), 7.38 (d, J=8.2 Hz, 2H), 7.33 (s, 1H), 6.57 (d, J=3.5 Hz, 1H), 2.36 (s, 3H) ppm.

Step 5b. 4-Bromo-6-methyl-1-tosyl-1,6-dihydro-7H-pyrrolo[2,3-c]pyridin-7-one (Compound 9)

A 60% dispersion of sodium hydride in mineral oil (NaH, 132 g, 3.3 moles, 1.2 equiv) was added portion-wise over 15 minutes to a solution of 4-bromo-1-tosyl-1H-pyrrolo-[2,3-c]pyridin-7-ol (Compound 14, 1000 g, 2.72 moles) in DMF (5 L). The temperature of the reaction mixture reached 39° C. After stirring for 30 minutes, the reaction mixture was cooled to 20° C. Iodomethane (MeI, 205 mL, 467 g, 3.3 moles, 1.2 equiv) was added and the reaction mixture was stirred at room temperature for 2.5 hours. When LCMS indicated the reaction was complete, water (13 L) was added and the reaction mixture was stirred for 30 minutes. The solids were filtered and washed sequentially with water (2.5 L) and heptanes (4 L). The solid was then dissolved in dichloromethane (DCM, 9 L) and the solution was transferred into a separation funnel. The residual water (~200 mL) was removed. The dichloromethane solution was treated with a mixture of sodium sulfate (Na₂SO₄, 200 g), silica gel (SiO₂, 170 g) and activated charcoal (20 g) for one hour. The solids were removed by filtration through a celite (750 g) pad and the celite pad was washed with dichloromethane (DCM, 3 L). Toluene (1.2 L) was added to the combined filtrates. The dichloromethane was removed under reduced pressure. The resulting solids in toluene were collected by filtration, washed sequentially with toluene (1.2 L) and heptanes (1.2 L), and dried under vacuum at 40° C. for 2 hours to give crude 4-bromo-6-methyl-1-tosyl-1,6-dihydro-7H-pyrrolo[2,3-c]pyridin-7-one (Compound 9, 728 g, 1036.9 g theoretical, 70.2% yield, 99.3% purity), which was used in the subsequent reaction without further purification. Compound 9: LCMS calculated for $C_{15}H_{13}BrN_2O_3S$ (M+H)⁺: 381.0, Found: 381.0; ¹H NMR (300 MHz, DMSO-d₆) δ 8.03 (m, 1H), 7.93 (m, 2H), 7.78 (s, 1H), 7.41 (m, 2H), 6.58 (m, 1H), 3.37 (s, 3H), 2.36 (s, 3H) ppm.

Synthesis of Compound 1 was carried out according to Scheme 3.

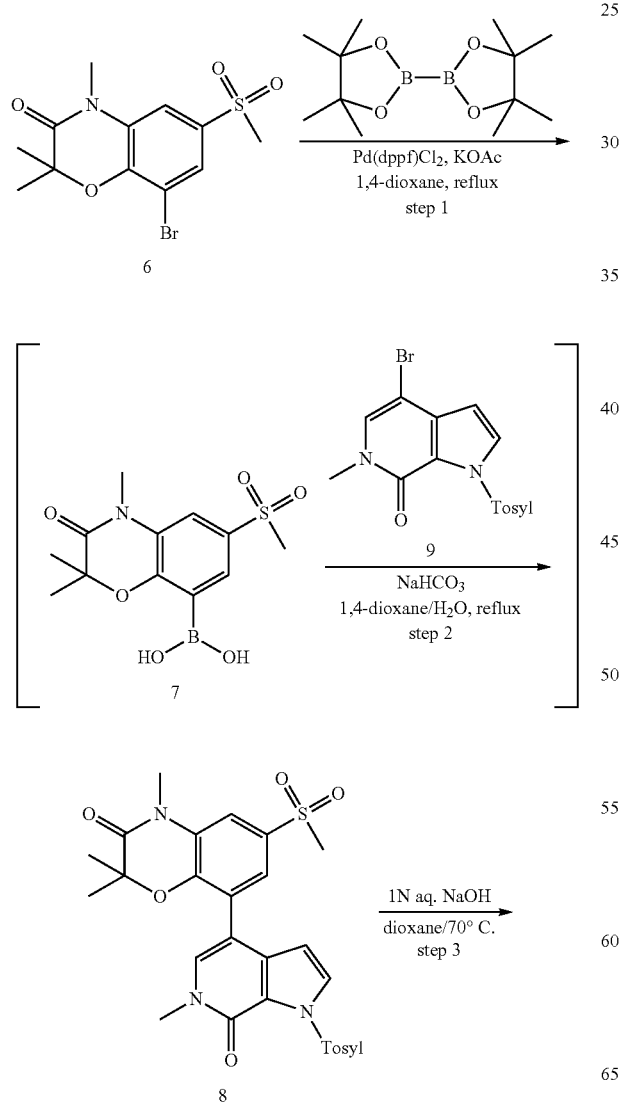

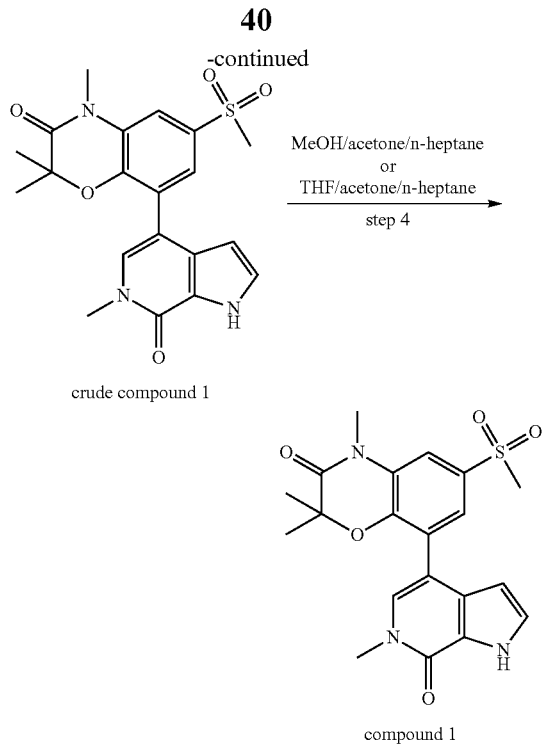

Steps 1 and 2. 2,2,4-Trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8)

A 100 L glass reactor was assembled with overhead stirring, thermocouple, addition funnel, and a nitrogen inlet and a 22 L glass reactor was assembled with overhead stirring, condenser, thermocouple, addition funnel, and a nitrogen inlet and each apparatus was purged with nitrogen. 1,4-Dioxane (15.8 L), 8-bromo-2,2,4-trimethyl-6-(methylsulfonyl)-2H-benzo[b][1,4]oxazin-3(4H)-one (Compound 6, 1008 g, 2.90 moles, 1.05 equiv), bis(pinacolato)diboron (1472 g, 5.80 moles, 2.11 equiv), and potassium acetate (KOAc, 854 g, 8.70 moles, 3.16 equiv) were charged to the 100 L reactor. Nitrogen was bubbled through the reaction mixture for 22 minutes and Pd(dppf)Cl₂—CH₂Cl₂ (60.08 g, 0.07 moles, 0.03 equiv) was charged and rinsed into the 100 L reactor with 1,4-dioxane (0.5 L). Nitrogen was bubbled through the reaction mixture again for 22 minutes. The resulting reaction mixture was heated to gentle reflux (about 81° C.) and stirred at reflux for about 19 hours until the first coupling reaction completion was indicated by HPLC. The reaction mixture was then cooled to about 28° C. Separately, a degassed aqueous sodium bicarbonate solution was prepared by thoroughly mixing sodium bicarbonate (NaHCO₃, 578 g, 6.89 moles, 2.50 equiv) and potable water (8.3 L) until a solution was obtained and then bubbling nitrogen through the solution for about 34 minutes. The degassed aqueous sodium bicarbonate solution and 4-bromo-6-methyl-1-tosyl-1H-pyrrolo[2,3-c]pyridin-7(6H)-one (Compound 9, 1050 g, 2.75 moles) were charged sequentially to the 100 L reactor at ambient temperature. The resulting reaction mixture in the 100 L reactor was heated to gentle reflux (about 89° C.) and stirred at reflux for about 2.5 hours until the second coupling reaction completion was indicated by HPLC. The reaction mixture was cooled to about 29° C.

before potable water (26.3 L) and ethyl acetate (EtOAc, 39.4 L) were charged. The mixture was stirred at ambient temperature for about 19 minutes before being filtered through a Celite (1050 g) bed. The filter cake was washed with ethyl acetate (EtOAc, 4.2 L). The filtrate and wash solution were charged back to the 100 L reactor, the phases were separated, and the organic phase was kept in the reactor. Separately, an aqueous sodium bisulfite solution was prepared by thoroughly mixing sodium bisulfite (17,052 g) and potable water (41.0 L). About one third of the aqueous sodium bisulfite solution (15.6 L) was charged to the organic solution in the 100 L reactor and the resulting mixture was heated to about 50° C. and stirred at about 54° C. for about 1 hour. The mixture was cooled to about 39° C. and filtered through the same Celite pad as before, and the filter cake was washed with ethyl acetate (4.2 L). The combined filtrate and wash solution were charged back to the 100 L reactor, the phases were separated, and the organic phase was kept in the reactor. About one third of the aqueous sodium bisulfite solution (15.6 L) was charged to the organic solution in the 100 L reactor and the resulting mixture was heated to about 50° C. and stirred at about 52° C. for about 1 hour. The reaction mixture was cooled to about 40° C., the phases were separated, and the organic phase was kept in the reactor. The remainder of the aqueous sodium bisulfite solution (15.6 L) was charged to the organic solution in the 100 L reactor and the resulting mixture was heated to about 50° C. and stirred at about 50° C. for about 1 hour. The mixture was cooled to about 40° C., the phases were separated, and the organic phase was kept in the reactor. The organic phase was washed sequentially with potable water (10.5 L) and aqueous sodium chloride solution prepared separately from 2100 g of sodium chloride and 10.5 L of potable water. The organic phase was concentrated under reduced pressure at about 42° C. to a target volume of 11 L remaining (10-12 L per kg of Compound 9 charged). The residue was transferred to the 22 L reactor. The organic phase was further concentrated under reduced pressure at about 52° C. to a target volume of 5 L remaining (5-6 L per kg of Compound 9 charged). The residue was cooled to about 24° C. and stirred at about 19° C. for about 11.5 hours. The solids were collected by filtration and the filter cake was washed with n-heptane (4.2 L) and air-dried for about 4 hours followed by further drying under vacuum at about 15-17° C. to afford crude 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 1232 g, 1566.5 g theoretical, 78.6% yield) as yellow to brown powder, which was combined with the other batches of the crude Compound 8 produced by the same procedures for the further purification as described below.

A 100 L glass reactor was assembled with overhead stirring, condenser, thermocouple, addition funnel, and a nitrogen inlet and the apparatus was purged with nitrogen. Methylene chloride (34 L) and crude 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 3400 g) were charged to the reactor and the mixture was stirred at about 17° C. until a solution was obtained. Si-Thiol (850 g) was charged to the resulting solution and the mixture was heated to about 31° C. and stirred at 31° C. for about 2.5 hours. The mixture was then cooled to about 20° C. before being filtered. The filter cake was washed with methylene chloride (14 L) and the combined filtrate and wash solution were concentrated under vacuum at about 32° C. to afford the purified 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 3728 g) as yellow to brown powder, which has with some organic solvents and was used directly in the subsequent reaction without further drying. Compound 8: $^1$H NMR (400 MHz, DMSO-$d_6$) δ 7.99 (dd, J=5.9, 2.3 Hz, 3H), 7.65 (d, J=2.0 Hz, 1H), 7.59 (d, J=2.0 Hz, 1H), 7.56 (s, 1H), 7.44 (d, J=8.2 Hz, 2H), 6.46 (d, J=3.5 Hz, 1H), 3.48 (s, 3H), 3.42 (s, 3H), 3.30 (s, 3H), 2.39 (s, 3H), 1.38 (s, 6H) ppm; $^{13}$C NMR (101 MHz, DMSO-$d_6$) δ 167.50 (s), 152.60 (s), 145.55 (s), 144.64 (s), 136.22 (s), 135.96 (s), 134.83 (s), 131.27 (s), 130.86 (s), 130.07 (s), 128.88 (s), 125.37 (s), 124.56 (s), 121.93 (s), 113.72 (s), 108.32 (s), 106.83 (s), 79.01 (s), 60.21 (s), 44.17 (s), 36.95 (s), 29.46 (s), 24.28 (s), 21.59 (s), 21.22 (s), 14.55 (s) ppm.

Step 3. 2,2,4-Trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one (Compound 1)

A 50 L glass reactor was assembled with overhead stirring, distillation apparatus, thermocouple, addition funnel, and a nitrogen inlet and the apparatus was purged with nitrogen. 1,4-Dioxane (10.2 L) and 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 3724 g resulted from the previous step and has solvents, 3400 g dry based, 5.97 moles) were charged to the reactor with stirring and the reaction mixture was heated to about 62° C. Separately, an aqueous sodium hydroxide solution was prepared by thoroughly mixing sodium hydroxide (NaOH, 860 g, 21.49 moles, 3.60 equiv) and potable water (21.5 L). The aqueous sodium hydroxide solution was charged to the reactor over about 26 minutes while maintaining the internal temperature at below 70° C. The reaction mixture was heated about 84° C. and stirred at about 84° C. for about 2.5 hours until the deprotection reaction completion was indicated by HPLC. The reaction mixture was distilled under reduced pressure at about 70° C. to a target volume of 17 L remaining (5 L per kg of Compound 8 charged). Potable water (13.6 L) was charged and the distillation was continued under reduced pressure at about 76° C. until an additional 7 L (2 L per kg of Compound 8 charged) was collected. The remaining mixture was cooled to about 25° C. and stirred at about 18° C. for about 11 hours. The solids were collected by filtration and the filter cake was washed with water (34 L) and dried on the filter for about 1 hour followed by air dried for about 5 days to afford crude 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one (compound 1, 1728 g, 2480 g theoretical, 69.7% yield), which was purified following the procedures described below.

A 50 L glass reactor was assembled with overhead stirring, thermocouple, and a nitrogen inlet and the apparatus was purged with nitrogen. Acetonitrile (17.2 L) and crude 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3(4H)-one (crude compound 1, 1726 g, 4.25 moles) were charged to the reactor with stirring. The resulting mixture was heated to about 72° C. and stirred at 70-75° C. for about 1.5 hours. The mixture was then cooled to about 25° C. and stirred at ambient temperature for about 1 hour. The solids were collected by filtration and the filter cake was washed with acetonitrile (9 L) before being charged back to the reactor with acetonitrile (17 L). The mixture was heated to about 39° C. and stirred at about 39° C. for about 1.5 hours. The mixture was cooled to about 17° C. and stirred at 17° C. for about 15 hours. The solids were collected by filtration and the filter cake was washed with methylene chloride (9 L). The product was dried on the filter for about 2 hours followed by air dried for about 1 day to afford the purified 2,2,4-trimethyl-8-(6-methyl-7-oxo-6,7-dihydro-1H-pyrrolo[2,3-c]pyridin-4-yl)-6-(methylsulfonyl)-2H-benzo [b][1,4]oxazin-3(4H)-one (compound 1, 1458 g, 1726 g theoretical, 84.5% yield), which was recrystallized to afford the desired crystalline form following the procedures described below.

Step 4. Recrystallization of 2,2,4-trimethyl-8-(6-methyl-7-oxo-6,7-dihydro-1H-pyrrolo[2,3-c]pyridin-4-yl)-6-(methylsulfonyl)-2H-benzo[b][1,4]oxazin-3 (4H)-one (Compound 1)

A 100 L glass reactor was assembled with overhead stirring, thermocouple, addition funnel, and a nitrogen inlet and a 50 L glass reactor was assembled with overhead stirring, condenser, thermocouple, addition funnel, and a nitrogen inlet and each apparatus was purged with nitrogen. Methanol (18.9 L), Compound 1 (1454 g), and acetone (18.9 L) were charged sequentially to the 100 L reactor with stirring. The resulting mixture was heated to about 57° C. and stirred at about 57° C. for about 1.25 hours until a clear solution was obtained. The mixture was transferred through an in-line filter into a clean 50 L reactor. The 100 L reactor and filter were rinsed with methanol (2.9 L) through the filter into the 50 L reactor. The mixture in the 50 L reactor was heated to about 52° C. and stirred at about 56° C. for about 7 minutes until a clear solution was obtained. The solution in the reactor was then concentrated under reduced pressure at about 58° C. to a target volume of 38 L remaining. The filtered n-heptane (37.7 L) was added to the reactor in portions while maintaining the internal temperature at below 60° C. The distillation under reduced pressure was continued at about 59° C. to a target volume of 22 L remaining. The remaining mixture was cooled to about 24° C. and stirred at about 17° C. for about 6.75 hours. The solids were collected by filtration and the filter cake was washed with the filtered n-heptane (7.3 L) and dried on the filter for about 1 hour followed by dried under vacuum at 60-65° C. to afford 2,2,4-trimethyl-8-(6-methyl-7-oxo-6,7-dihydro-1H-pyrrolo [2,3-c]pyridin-4-yl)-6-(methylsulfonyl)-2H-benzo[b][1,4] oxazin-3(4H)-one (compound 1, 1404 g, 1454 g theoretical, 96.6%) as white to off-white crystalline (Form I) powders. Compound 1: mp 266.4° C.; $^1$H NMR (400 MHz, DMSO-$d_6$) δ 12.13 (s, 1H), 7.67 (d, J=1.9 Hz, 1H), 7.62 (d, J=1.9 Hz, 1H), 7.33 (s, 2H), 6.19 (s, 1H), 3.59 (s, 3H), 3.43 (s, 3H), 3.31 (s, 3H), 1.41 (s, 6H) ppm; $^{13}$C NMR (101 MHz, DMSO-$d_6$) δ 167.66 (s), 154.57 (s), 144.55 (s), 134.74 (s), 130.96 (s), 130.33 (s), 129.68 (s), 127.40 (s), 126.96 (s), 124.39 (s), 123.53 (s), 113.15 (s), 109.35 (s), 103.07 (s), 78.80 (s), 44.22 (s), 36.15 (s), 29.46 (s), 24.26 (s) ppm.

Recrystallization conducted in a mixture of tetrahydrofuran (THF), acetone, and n-heptane using similar procedures as above afford Form II of the crystalline Compound 1 drug substance was obtained. Both Form I and Form II have very sharp melting endotherm peaks on DSC, and the two forms are about one degree difference in peak melting temperature: 266.4° C. for Form I and 267.5° C. for Form II. However, Form I and Form II have very different XRD patterns, but both are stable in aqueous suspension. Studies revealed that Form I is the most stable form in MeOH and acetone while Form II is more stable in IPA. In a mixture of methanol, acetone, and n-heptane, Form I and Form II could be interconverted to each other depending on the conditions such as solvent ratio, temperature, and time. Form I and Form II of the crystalline Compound 1 have similar solubility in organic solvents and water.

Form I can also be obtained by adding about 30 mg of Compound 1 to about 2 mL of saturated or cloudy solution of Compound 1 in acetone followed by stirring at 25±1° C. for 3 days.

An alternative synthesis of Compound 8 was carried out according to Scheme 4.

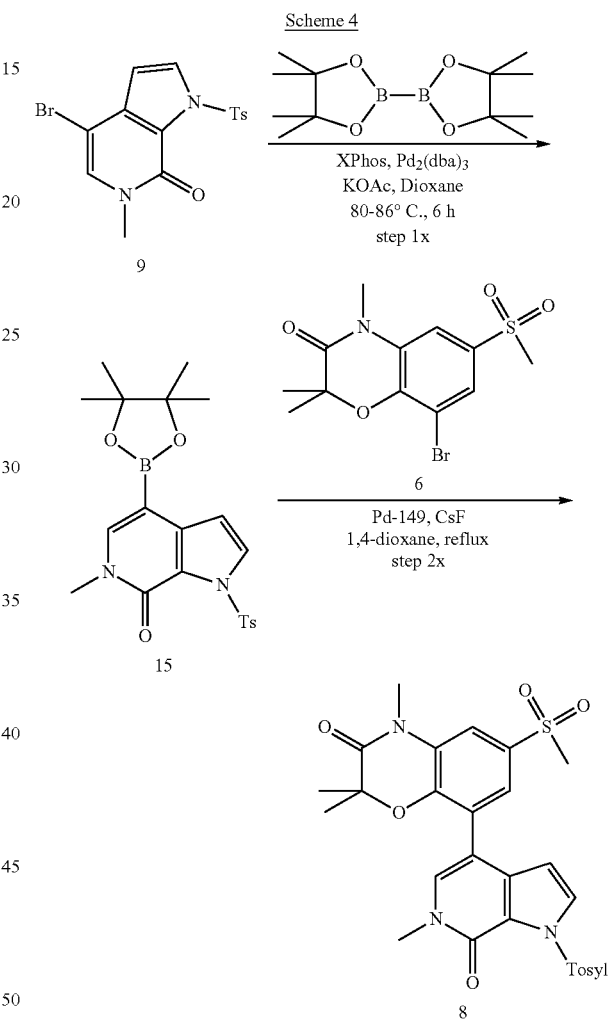

Scheme 4

Step 1x. 6-Methyl-4-(4,4,5,5-tetramethyl-1,3,2-dioxaborolan-2-yl)-1-tosyl-1H-pyrrolo[2,3-c]pyridin-7 (6H)-one (Compound 15)

A 500-mL three-necked round-bottomed flask was equipped with a condenser and a nitrogen inlet, which consists of a T-tube assembly connected to a mineral oil bubbler. 4-Bromo-6-methyl-1-[(4-methylphenyl) sulfonyl]-1,6-dihydro-7H-pyrrolo[2,3-c]pyridin-7-one (Compound 9, 10.0 g, 26.2 mmol), 4,4,4',4',5,5,5',5'-octamethyl-2,2'-bi(1, 3,2-dioxaborolane) (13 g, 52 mmol, 2.0 equiv), dicyclohexyl (2',4',6'-triisopropylbiphenyl-2-yl)phosphine (Xphos, 1.2 g, 2.6 mmol, 0.1 equiv), potassium acetate (5.66 g, 57.7 mmol, 2.2 equiv), and 1,4-dioxane (110 mL) were charged into the flask. The mixture was degassed with nitrogen for 5 min. before tris(dibenzylideneacetone)dipalladium(0) (Pd$_2$(dba)$_3$, 600 mg, 0.656 mmol, 0.025 equiv) was added to the mixture and the nitrogen degassing was continued for 1-2 min. The reaction mixture was then heated to 80° C. and stirred at 80-86° C. for 19 h. When HPLC indicated the reaction was complete, the reaction mixture was cooled to room temperature. 2-Methoxy-2-methylpropane (MTBE, 50 mL) and silica gel (SiO$_2$, 8 g) were added and the mixture was stirred at room temperature for 30 min. The mixture was filtered through a pad of silica gel and the silica gel pad was washed with MTBE. The combined filtrates were concentrated under reduced pressure and the residue was purified by flash column (silica gel, a gradient of 0-80% EtOAc in hexanes) to afford 6-methyl-4-(4,4,5,5-tetramethyl-1,3,2-dioxaborolan-2-yl)-1-tosyl-1H-pyrrolo[2,3-c]pyridin-7(6H)-one (Compound 15, 9.5 g, 11.22 g theoretical, 84.7%) as a brown to red oil, which was solidified upon standing at room temperature under vacuum. Compound 15: LCMS calculated for C$_{21}$H$_{25}$BN$_2$O$_5$S (M+H)$^+$, (2M+Na)$^+$: m/z 429.3, 879.3; Found: 429.1, 879.3.

Step 2x. 2,2,4-Trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8)

A solution of 8-bromo-2,2,4-trimethyl-6-(methylsulfonyl)-2H-1,4-benzoxazin-3(4H)-one (Compound 6, 22.4 g, 64.5 mmol) and 6-methyl-4-(4,4,5,5-tetramethyl-1,3,2-dioxaborolan-2-yl)-1-tosyl-1H-pyrrolo[2,3-c]pyridin-7(6H)-one (Compound 15, 29.0 g, 67.7 mmol, 1.05 equiv) in 1,4-dioxane (350 mL) and water (80 mL) was treated with cesium fluoride (CsF, 33.9 g, 223 mmol, 3.46 equiv) and 4-(di-tert-butylphosphino)-N,N-dimethylaniline-dichloropalladium (2:1) (2.0 g, 2.8 mmol, 0.043 equiv) at ambient temperature. The resulting reaction mixture was then degassed three times and each time filled with a steady stream of nitrogen gas. The reaction mixture was then heated to reflux for 2-3 hours. Once HPLC showed the coupling reaction was complete, the reaction mixture was gradually cooled down to 30° C. before water (300 mL) and 2-methoxy-2-methylpropane (MTBE, 300 mL) were added. The mixture was then stirred at ambient temperature for 15 min before the two layers were separated. The aqueous layer was extracted with methoxy-2-methylpropane (MTBE, 100 mL). The combined extracts were treated with a solution of sodium bisulfite (40 g) in water (200 mL) and the resulting mixture was stirred at ambient temperature for 2 hours. The solids were collected by filtration, washed with water, and dried in vacuum oven overnight to give the first crop of the desired product, 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 20.0 g, 36.74 g theoretical, 54.4% yield), as off-white to yellow powder, which was used directly in the subsequent reaction without further purification.

The two layers of the filtrate were separated, and the organic layer was dried over MgSO$_4$ and concentrated under reduced pressure. The residue was then purified by column chromatography (SiO$_2$, gradient elution with 40-100% EtOAc in hexanes) to give the second crop of the desired compound, 2,2,4-trimethyl-8-(6-methyl-7-oxo-1-tosyl-6,7-dihydro-1H-pyrrolo[2,3-c]pyridin-4-yl)-6-(methylsulfonyl)-2H-benzo[b][1,4]oxazin-3(4H)-one (Compound 8, 13.8 g, 36.74 g theoretical, 37.5 yield; total 33.8 g, 91.9 yield), as a pink oil, which was solidified at room temperature under vacuum and was used directly in the subsequent reaction without further purification.

Batches of Compound 8 produced by this alternative synthetic process has been found to be identical to the material produced by the original synthesis as described in Scheme 3. This material was subsequently converted to Compound 1 by following the same procedures described in Scheme 3.

Example 2. X-Ray Powder Diffraction (XRPD) Studies for Form I and Form II

Form I and Form II of Compound 1 were characterized by XRPD. The XRPD was obtained from Bruker D2 PHASER X-ray Powder Diffractometer instrument. The general experimental procedures for XRPD were: (1) X-ray radiation from copper at 1.054056 Å with K$_\beta$ filter and LYNX-EYE™ detector; (2) X-ray power at 30 kV, 10 mA; and (3) the sample powder was dispersed on a zero-background sample holder. The general measurement conditions for XRPD were: Start Angle 5 degrees; Stop Angle 30 degrees; Sampling 0.015 degrees; and Scan speed 2 degree/min.

The XRPD pattern of Form I is shown in FIG. 1 and the XRPD data are provided in Table 1.

TABLE 1

| Form I | | |
|---|---|---|
| 2-Theta (°) | Height | H % |
| 7.9 | 103 | 0.3 |
| 8.7 | 16238 | 43.3 |
| 9.8 | 18668 | 49.8 |
| 10.0 | 367 | 1.0 |
| 10.2 | 214 | 0.6 |
| 10.5 | 137 | 0.4 |
| 11.6 | 9126 | 24.3 |
| 11.9 | 2024 | 5.4 |
| 12.0 | 1846 | 4.9 |
| 12.7 | 37515 | 100 |
| 13.6 | 1284 | 3.4 |
| 14.0 | 5077 | 13.5 |
| 14.7 | 7636 | 20.4 |
| 15.7 | 13471 | 35.9 |
| 17.5 | 4552 | 12.1 |
| 17.7 | 2920 | 7.8 |
| 18.1 | 1194 | 3.2 |
| 18.3 | 3113 | 8.3 |
| 19.2 | 1170 | 3.1 |
| 19.4 | 657 | 1.8 |
| 20.0 | 8378 | 22.3 |
| 21.4 | 20976 | 55.9 |
| 21.9 | 2044 | 5.4 |
| 22.5 | 6047 | 16.1 |
| 23.3 | 17466 | 46.6 |
| 23.7 | 724 | 1.9 |
| 24.2 | 171 | 0.5 |
| 25.3 | 394 | 1.0 |
| 25.4 | 469 | 1.3 |
| 26.2 | 2777 | 7.4 |
| 26.5 | 1191 | 3.2 |
| 27.1 | 8100 | 21.6 |
| 28.2 | 1893 | 5.0 |
| 28.8 | 2412 | 6.4 |
| 29.2 | 460 | 1.2 |
| 29.3 | 533 | 1.4 |
| 29.5 | 373 | 1.0 |

The XRPD pattern of Form II of Compound 1 is shown in FIG. 4 and the XRPD data are provided in Table 2.

TABLE 2

| 2-Theta (°) | Height | H % |
|---|---|---|
| 6.7 | 6755 | 9.3 |
| 9.4 | 2759 | 3.8 |
| 9.5 | 5697 | 7.9 |
| 10.5 | 3305 | 4.6 |
| 13.3 | 1509 | 2.1 |
| 14.8 | 15378 | 21.3 |
| 15.1 | 1751 | 2.4 |
| 15.3 | 630 | 0.9 |
| 15.7 | 1367 | 1.9 |
| 16.2 | 22052 | 30.5 |
| 17.0 | 72319 | 100 |
| 17.1 | 46591 | 64.4 |
| 18.2 | 1945 | 2.7 |
| 18.8 | 12556 | 17.4 |
| 19.3 | 36093 | 49.9 |
| 19.7 | 8478 | 11.7 |
| 20.5 | 5565 | 7.7 |
| 21.3 | 2569 | 3.6 |
| 21.4 | 995 | 1.4 |
| 21.6 | 740 | 1.0 |
| 22.0 | 135 | 0.2 |
| 23.1 | 7421 | 10.3 |
| 23.8 | 7448 | 10.3 |
| 24.4 | 3308 | 4.6 |
| 24.7 | 3946 | 5.5 |
| 25.2 | 3538 | 4.9 |
| 25.3 | 4287 | 5.9 |
| 25.7 | 436 | 0.6 |
| 26.4 | 3710 | 5.1 |
| 26.8 | 548 | 0.8 |
| 27.5 | 9253 | 12.8 |
| 28.3 | 2614 | 3.6 |
| 28.5 | 7520 | 10.4 |
| 29.0 | 2591 | 3.6 |
| 29.8 | 1322 | 1.8 |
| 30.4 | 4664 | 6.4 |

Example 3. Differential Scanning Calorimetry (DSC) Studies for Form I and Form II Form I and Form II of Compound 1 were characterized by DSC. The DSC was obtained from TA Instruments Differential Scanning calorimetry, Model Q2000 with autosampler. The DSC instrument conditions were as follows: 25-300° C. at 10° C./min; Tzero aluminum sample pan and lid; and nitrogen gas flow at 50 mL/min.

The DSC thermogram of Form I is shown in FIG. 2. The DSC thermogram of Form I revealed a major endothermic event at an onset temperature of 264.7° C. with a peak temperature of 266.4° C. which is believed to be the melting/decomposition of the compound.

The DSC thermogram of Form II is shown in FIG. 5. The DSC thermogram of Form II revealed a major endothermic event at an onset temperature of 266.7° C. with a peak temperature of 267.5° C. which is believed to be the melting/decomposition of the compound.

Example 4. Thermogravimetric Analysis (TGA) Studies for Form I and II

Form I and Form II of Compound 1 were characterized by TGA. The TGA was obtained from PerkinElmer Thermogravimetric Analyzer, Model Pyris 1. The general experimental conditions for TGA were: ramp from 25° C. to 350° C. at 10° C./min; nitrogen purge gas flow at 60 mL/min; ceramic crucible sample holder.

The TGA thermogram of Form I is shown in FIG. 3. A weight loss of about 0.4% up to 150° C. was observed and believed to be associated with the loss of moisture or residual solvents. Significant weight loss above 250° C. was observed and believed to be associated with the decomposition of the compound.

The TGA thermogram of Form II is shown in FIG. 6. Significant weight loss above 250° C. was observed and believed to be associated with the decomposition of the compound.

Example 5. Preparation of Forms Ia, III, IV, V, Va, VI, VII, VIII, IX, X, XI, XII, XIII, XIV, and XV and Amorphous Compound 1

Forms Ia, III, IV, V, Va, VI, VII, VIII, IX, X, XI, XII, XIII, XIV, and XV and Amorphous of Compound 1 were prepared according to the procedures in Table 3 below. These forms were analyzed by XRPD (see Example 6), DSC (see Example 7), and TGA (see Example 8).

TABLE 3

| Solid state form before drying | Procedures |
|---|---|
| Form Ia | To 16 mL of heptane was added 4 mL of saturated solution of Compound 1 in acetone followed by stirring to give a solid. |
| Form III | To about 2 mL of saturated or cloudy solution of Compound 1 in acetonitrile was added about 30 mg of Compound 1 followed by stirring at 25 ± 1° C. for 3 days. |
| Form IV | To about 2 mL of saturated or cloudy solution of Compound 1 in DCM was added about 30 mg of Compound 1 followed by stirring at 25 ± 1° C. for 3 days. |
| Form V | To about 2 mL of saturated or cloudy solution of Compound 1 in 1,4-dioxane was added about 30 mg of Compound 1 followed by stirring at 25 ± 1° C. for 3 days. |
| Form Va | To 4.0 mL of saturated solution of Compound 1 in 1,4-dioxane was added 16 mL of hexane followed by stirring to give a solid. |
| Form VI | To about 2 mL of saturated or cloudy solution of Compound 1 in methanol was added about 30 mg of Compound 1 followed by stirring at 25 ± 1° C. for 3 days. |
| Form VII | To about 2 mL of saturated or cloudy solution of Compound 1 in 2-methoxyethanol was added about 30 mg of Compound 1 followed by stirring at 25 ± 1° C. for 3 days. |
| Form VIII | Approximately 6 mL of saturated solution of Compound 1 in THF was evaporated under air without stirring at 50 ± 1° C. |
| Form IX | To about 2 mL of saturated or cloudy solution of Compound 1 in ethyl acetate was added about 30 mg of Compound 1 followed by stirring at 25 ± 1° C. for 3 days. |

TABLE 3-continued

| Solid state form before drying | Procedures |
|---|---|
| Form X | To about 2 mL of saturated or cloudy solution of Compound 1 in 2-methoxyethanol was added about 30 mg of Compound 1 followed by stirring at 50 ± 1° C. for 2 days. |
| Form XI | Approximately 3-4 mL of saturated solution of Compound 1 in chloroform was evaporated under air without stirring at 25 ± 1° C. |
| Form XII | Approximately 10 mL of saturated solution of Compound 1 in 1-propanol was evaporated under air without stirring at 50 ± 1° C. |
| Form XIII | To 4 mL of saturated solution of Compound 1 in acetone was added 16 mL of heptane followed by stirring to give a solid. |
| Form XIV | To 4 mL of saturated solution of Compound 1 in acetone was added 16 mL of hexane followed by stirring to give a solid. |
| Form XV | The sample from Form III was dried under vacuum at 45-50° C. for 28 h. |
| Amorphous | Approximately 3.5 mL of saturated solution of Compound 1 in 1,4-dioxane were evaporated under air without stirring at 25 ± 1° C. to give a solid. |

Example 6. XRPD of Forms Ia, III, IV, V, Va, VI, VII, VIII, IX, X, XI, XII, XIII, XIV, and XV and Amorphous XRPD studies were conducted on the various forms from Example 5. The X-Ray Powder Diffraction (XRPD) was obtained from Rigaku MiniFlex X-ray Powder Diffractometer (XRPD). The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

FIGS. 7-21 are XRPD patterns of Forms Ia, III, IV, V, Va, VI, VII, VIII, IX, X, XI, XII, XIII, XIV, and XV, respectively. Tables 4-18 are peak listings of Forms Ia, III, IV, V, Va, VI, VII, VIII, IX, X, XI, XII, XIII, XIV, and XV, respectively. The amorphous solid from Example 6 was analyzed using XRPD and determined to be amorphous.

TABLE 4

Form Ia

| 2-Theta (°) | Height | H % |
|---|---|---|
| 7.8 | 55 | 9.9 |
| 8.8 | 325 | 58.5 |
| 10.0 | 361 | 64.9 |
| 11.7 | 140 | 25.2 |
| 12.8 | 556 | 100 |
| 13.5 | 513 | 92.3 |
| 14.1 | 99 | 17.8 |
| 15.8 | 89 | 16.0 |
| 16.8 | 65 | 11.7 |
| 17.7 | 116 | 20.9 |
| 20.0 | 329 | 59.2 |
| 20.9 | 98 | 17.6 |
| 21.5 | 271 | 48.7 |
| 22.3 | 417 | 75.0 |
| 22.6 | 556 | 100 |
| 23.3 | 227 | 40.8 |
| 27.2 | 187 | 33.6 |
| 28.3 | 36 | 6.5 |
| 28.9 | 93 | 16.7 |
| 31.8 | 52 | 9.4 |
| 35.6 | 58 | 10.4 |

TABLE 5

Form III

| 2-Theta (°) | Height | H % |
|---|---|---|
| 7.8 | 201 | 26.0 |
| 12.4 | 403 | 52.2 |
| 13.1 | 181 | 23.4 |
| 15.2 | 297 | 38.5 |
| 15.5 | 435 | 56.3 |
| 16.9 | 688 | 89.1 |
| 17.5 | 772 | 100 |
| 19.1 | 53 | 6.9 |
| 20.3 | 551 | 71.4 |
| 21.0 | 67 | 8.7 |
| 21.9 | 70 | 9.1 |
| 22.8 | 170 | 22.0 |
| 23.5 | 64 | 8.3 |
| 24.1 | 143 | 18.5 |
| 24.5 | 218 | 28.2 |
| 25.0 | 167 | 21.6 |
| 26.9 | 327 | 42.4 |
| 28.7 | 74 | 9.6 |
| 29.4 | 121 | 15.7 |
| 30.5 | 94 | 12.2 |
| 31.1 | 53 | 6.9 |
| 31.9 | 45 | 5.8 |
| 32.6 | 43 | 5.6 |
| 33.4 | 70 | 9.1 |
| 37.3 | 77 | 10.0 |
| 42.8 | 85 | 11.0 |
| 43.2 | 45 | 5.8 |

TABLE 6

Form IV

| 2-Theta (°) | Height | H % |
|---|---|---|
| 7.0 | 80 | 9.4 |
| 9.4 | 97 | 11.4 |
| 10.0 | 71 | 8.4 |
| 11.2 | 167 | 19.6 |
| 16.3 | 246 | 28.9 |
| 17.5 | 125 | 14.7 |
| 18.7 | 196 | 23.1 |
| 20.7 | 107 | 12.6 |
| 22.1 | 850 | 100 |
| 23.8 | 85 | 10.0 |
| 25.6 | 92 | 10.8 |
| 26.2 | 133 | 15.6 |
| 26.8 | 232 | 27.3 |

TABLE 6-continued

Form IV

| 2-Theta (°) | Height | H % |
|---|---|---|
| 29.0 | 75 | 8.8 |
| 30.0 | 78 | 9.2 |
| 35.5 | 75 | 8.8 |
| 41.9 | 51 | 6.0 |

TABLE 7

Form V

| 2-Theta (°) | Height | H % |
|---|---|---|
| 8.2 | 452 | 31.9 |
| 8.5 | 510 | 36.0 |
| 14.1 | 225 | 15.9 |
| 16.3 | 764 | 54.0 |
| 17.1 | 1416 | 100 |
| 17.8 | 127 | 9.0 |
| 18.9 | 293 | 20.7 |
| 19.8 | 895 | 63.2 |
| 21.4 | 114 | 8.1 |
| 21.8 | 337 | 23.8 |
| 22.7 | 218 | 15.4 |
| 23.8 | 70 | 4.9 |
| 24.6 | 127 | 9.0 |
| 25.8 | 369 | 26.1 |
| 27.0 | 41 | 2.9 |
| 27.6 | 327 | 23.1 |
| 28.5 | 49 | 3.5 |
| 29.4 | 131 | 9.3 |
| 29.9 | 290 | 20.5 |
| 32.6 | 257 | 18.1 |
| 33.1 | 71 | 5.0 |
| 33.6 | 38 | 2.7 |
| 34.6 | 60 | 4.2 |
| 37.8 | 35 | 2.5 |
| 38.2 | 56 | 4.0 |
| 38.6 | 61 | 4.3 |
| 39.9 | 57 | 4.0 |
| 40.9 | 39 | 2.8 |
| 41.7 | 66 | 4.7 |
| 43.2 | 78 | 5.5 |
| 43.6 | 73 | 5.2 |
| 44.2 | 44 | 3.1 |

TABLE 8

Form Va

| 2-Theta (°) | Height | H % |
|---|---|---|
| 8.7 | 328 | 38.2 |
| 9.8 | 55 | 6.4 |
| 12.8 | 63 | 7.3 |
| 14.1 | 51 | 5.9 |
| 16.5 | 307 | 35.7 |
| 17.3 | 859 | 100 |
| 19.1 | 61 | 7.1 |
| 19.9 | 222 | 25.8 |
| 20.4 | 123 | 14.3 |
| 21.6 | 115 | 13.4 |
| 23.4 | 48 | 5.6 |
| 24.8 | 37 | 4.3 |
| 25.9 | 122 | 14.2 |
| 27.6 | 93 | 10.8 |
| 29.9 | 65 | 7.6 |
| 32.7 | 68 | 7.9 |
| 43.8 | 38 | 4.4 |

TABLE 9

Form VI

| 2-Theta (°) | Height | H % |
|---|---|---|
| 4.0 | 156 | 9.3 |
| 8.5 | 828 | 49.4 |
| 9.6 | 485 | 29.0 |
| 11.4 | 379 | 22.6 |
| 12.1 | 1553 | 92.7 |
| 13.5 | 548 | 32.7 |
| 14.5 | 460 | 27.5 |
| 15.2 | 696 | 41.6 |
| 17.1 | 643 | 38.4 |
| 17.7 | 804 | 48.0 |
| 18.1 | 242 | 14.4 |
| 19.2 | 587 | 35.0 |
| 20.7 | 1675 | 100 |
| 21.8 | 467 | 27.9 |
| 22.6 | 1467 | 87.6 |
| 23.2 | 684 | 40.8 |
| 23.9 | 178 | 10.6 |
| 25.1 | 322 | 19.2 |
| 26.1 | 878 | 52.4 |
| 28.1 | 163 | 9.7 |
| 29.3 | 181 | 10.8 |
| 30.7 | 450 | 26.9 |
| 32.1 | 79 | 4.7 |
| 33.3 | 190 | 11.3 |
| 35.7 | 140 | 8.4 |
| 36.5 | 81 | 4.8 |
| 38.1 | 147 | 8.8 |
| 41.4 | 148 | 8.8 |
| 42.6 | 122 | 7.3 |

TABLE 10

Form VII

| 2-Theta (°) | Height | H % |
|---|---|---|
| 9.9 | 678 | 12.5 |
| 12.2 | 1889 | 34.8 |
| 14.8 | 1009 | 18.6 |
| 15.7 | 666 | 12.3 |
| 16.6 | 298 | 5.5 |
| 17.0 | 2239 | 41.3 |
| 17.5 | 1807 | 33.3 |
| 17.9 | 236 | 4.4 |
| 18.2 | 84 | 1.5 |
| 18.8 | 5422 | 100 |
| 19.2 | 538 | 9.9 |
| 19.5 | 377 | 7.0 |
| 20.2 | 1103 | 20.3 |
| 20.8 | 1072 | 19.8 |
| 21.9 | 1920 | 35.4 |
| 22.5 | 207 | 3.8 |
| 22.9 | 752 | 13.9 |
| 23.3 | 503 | 9.3 |
| 23.7 | 254 | 4.7 |
| 24.3 | 131 | 2.4 |
| 24.6 | 1330 | 24.5 |
| 25.6 | 2990 | 55.1 |
| 26.6 | 632 | 11.7 |
| 27.9 | 612 | 11.3 |
| 28.4 | 491 | 9.1 |
| 28.8 | 54 | 1.0 |
| 29.3 | 111 | 2.0 |
| 30.0 | 342 | 6.3 |
| 30.9 | 130 | 2.4 |
| 31.5 | 240 | 4.4 |
| 32.0 | 385 | 7.1 |
| 32.4 | 373 | 6.9 |
| 32.9 | 198 | 3.7 |
| 33.3 | 222 | 4.1 |
| 33.8 | 478 | 8.8 |
| 34.5 | 480 | 8.9 |
| 35.7 | 236 | 4.4 |

TABLE 10-continued

Form VII

| 2-Theta (°) | Height | H % |
| --- | --- | --- |
| 37.0 | 217 | 4.0 |
| 37.7 | 91 | 1.7 |
| 38.2 | 287 | 5.3 |
| 39.0 | 109 | 2.0 |
| 39.6 | 124 | 2.3 |
| 40.6 | 333 | 6.1 |
| 42.4 | 343 | 6.3 |
| 43.0 | 144 | 2.7 |
| 44.2 | 544 | 10.0 |

TABLE 11

Form VIII

| 2-Theta (°) | Height | H % |
| --- | --- | --- |
| 4.3 | 148 | 16.6 |
| 8.1 | 892 | 100 |
| 8.5 | 686 | 76.9 |
| 13.9 | 43 | 4.8 |
| 16.2 | 713 | 79.9 |
| 16.6 | 143 | 16.0 |
| 17.0 | 891 | 99.9 |
| 17.5 | 97 | 10.9 |
| 18.0 | 158 | 17.7 |
| 18.9 | 111 | 12.4 |
| 19.6 | 664 | 74.4 |
| 20.1 | 226 | 25.3 |
| 20.5 | 80 | 9.0 |
| 21.5 | 89 | 10.0 |
| 21.8 | 249 | 27.9 |
| 22.8 | 47 | 5.3 |
| 23.7 | 82 | 9.2 |
| 24.4 | 117 | 13.1 |
| 25.6 | 194 | 21.7 |
| 26.3 | 41 | 4.6 |
| 27.4 | 101 | 11.3 |
| 29.3 | 84 | 9.4 |
| 29.7 | 92 | 10.3 |
| 30.3 | 36 | 4.0 |
| 32.4 | 138 | 15.5 |
| 32.7 | 71 | 8.0 |
| 33.4 | 27 | 3.0 |
| 33.8 | 29 | 3.3 |
| 34.1 | 37 | 4.1 |
| 36.2 | 45 | 5.0 |
| 37.5 | 30 | 3.4 |
| 38.3 | 33 | 3.7 |
| 40.7 | 30 | 3.4 |
| 41.0 | 30 | 3.4 |
| 42.5 | 31 | 3.5 |
| 43.3 | 48 | 5.4 |

TABLE 12

Form IX

| 2-Theta (°) | Height | H % |
| --- | --- | --- |
| 8.6 | 182 | 20.8 |
| 9.1 | 194 | 22.1 |
| 11.4 | 301 | 34.4 |
| 13.4 | 192 | 21.9 |
| 15.2 | 212 | 24.2 |
| 16.1 | 38 | 4.3 |
| 17.1 | 74 | 8.4 |
| 18.2 | 827 | 94.4 |
| 19.1 | 89 | 10.2 |
| 20.6 | 57 | 6.5 |
| 22.1 | 681 | 77.7 |
| 22.8 | 378 | 43.2 |

TABLE 12-continued

Form IX

| 2-Theta (°) | Height | H % |
| --- | --- | --- |
| 23.9 | 876 | 100 |
| 24.3 | 329 | 37.6 |
| 25.0 | 89 | 10.2 |
| 26.9 | 156 | 17.8 |
| 27.3 | 54 | 6.2 |
| 28.2 | 43 | 4.9 |
| 28.9 | 60 | 6.8 |
| 29.5 | 75 | 8.6 |
| 30.8 | 117 | 13.4 |
| 31.3 | 44 | 5.0 |
| 32.0 | 85 | 9.7 |
| 35.3 | 114 | 13.0 |
| 35.9 | 31 | 3.5 |
| 36.6 | 63 | 7.2 |
| 40.0 | 59 | 6.7 |
| 40.7 | 44 | 5.0 |

TABLE 13

Form X

| 2-Theta (°) | Height | H % |
| --- | --- | --- |
| 4.6 | 133 | 0.7 |
| 9.8 | 70 | 0.4 |
| 12.2 | 144 | 0.7 |
| 12.4 | 235 | 1.2 |
| 14.9 | 441 | 2.2 |
| 15.3 | 611 | 3.1 |
| 15.8 | 554 | 2.8 |
| 17.0 | 19729 | 100 |
| 17.7 | 1273 | 6.5 |
| 18.3 | 1632 | 8.3 |
| 18.9 | 299 | 1.5 |
| 19.7 | 2260 | 11.5 |
| 20.3 | 488 | 2.5 |
| 20.7 | 352 | 1.8 |
| 20.9 | 612 | 3.1 |
| 21.5 | 104 | 0.5 |
| 22.1 | 126 | 0.6 |
| 22.5 | 111 | 0.6 |
| 22.9 | 270 | 1.4 |
| 23.5 | 602 | 3.1 |
| 24.6 | 141 | 0.7 |
| 24.8 | 412 | 2.1 |
| 25.4 | 1339 | 6.8 |
| 26.1 | 198 | 1.0 |
| 26.8 | 195 | 1.0 |
| 27.5 | 160 | 0.8 |
| 27.9 | 210 | 1.1 |
| 29.0 | 133 | 0.7 |
| 30.0 | 67 | 0.3 |
| 30.4 | 217 | 1.1 |
| 30.7 | 194 | 1.0 |
| 31.0 | 127 | 0.6 |
| 31.7 | 83 | 0.4 |
| 32.3 | 3996 | 20.3 |
| 34.0 | 4210 | 21.3 |
| 34.8 | 279 | 1.4 |
| 37.0 | 1123 | 5.7 |
| 37.5 | 270 | 1.4 |
| 37.8 | 76 | 0.4 |
| 38.4 | 336 | 1.7 |
| 39.4 | 684 | 3.5 |
| 39.8 | 275 | 1.4 |
| 40.6 | 279 | 1.4 |
| 40.9 | 1191 | 6.0 |
| 41.7 | 2101 | 10.6 |
| 42.5 | 173 | 0.9 |
| 43.2 | 71 | 0.4 |

TABLE 13-continued

| Form X | | |
|---|---|---|
| 2-Theta (°) | Height | H % |
| 43.9 | 258 | 1.3 |
| 44.3 | 475 | 2.4 |
| 44.6 | 134 | 0.7 |

TABLE 14

| Form XI | | |
|---|---|---|
| 2-Theta (°) | Height | H % |
| 7.7 | 95 | 18.0 |
| 8.8 | 193 | 36.5 |
| 9.6 | 86 | 16.3 |
| 10.8 | 80 | 15.1 |
| 12.8 | 265 | 50.1 |
| 14.7 | 73 | 13.8 |
| 15.8 | 127 | 24.0 |
| 18.0 | 376 | 71.1 |
| 20.6 | 288 | 54.4 |
| 21.5 | 442 | 83.6 |
| 22.6 | 268 | 50.7 |
| 23.3 | 529 | 100 |
| 26.4 | 181 | 34.2 |
| 27.3 | 168 | 31.8 |
| 31.6 | 105 | 19.8 |

TABLE 15

| Form XII | | |
|---|---|---|
| 2-Theta (°) | Height | H % |
| 3.9 | 215 | 11.7 |
| 5.6 | 1112 | 60.3 |
| 8.5 | 52 | 2.8 |
| 11.2 | 93 | 5.0 |
| 11.7 | 448 | 24.3 |
| 12.5 | 45 | 2.4 |
| 13.8 | 553 | 30.0 |
| 14.5 | 591 | 32.0 |
| 16.3 | 58 | 3.1 |
| 16.9 | 299 | 16.2 |
| 17.7 | 304 | 16.5 |
| 18.7 | 966 | 52.4 |
| 19.9 | 52 | 2.8 |
| 21.4 | 87 | 4.7 |
| 21.8 | 99 | 5.4 |
| 23.5 | 202 | 10.9 |
| 24.6 | 476 | 25.8 |
| 25.7 | 79 | 4.3 |
| 27.0 | 37 | 2.0 |
| 27.7 | 55 | 3.0 |
| 29.3 | 70 | 3.8 |
| 30.1 | 68 | 3.7 |
| 31.6 | 41 | 2.2 |
| 34.3 | 294 | 15.9 |
| 39.8 | 68 | 3.7 |
| 42.9 | 38 | 2.1 |
| 44.2 | 1845 | 100 |
| 44.6 | 1468 | 79.6 |

TABLE 16

| Form XIII | | |
|---|---|---|
| 2-Theta (°) | Height | H % |
| 5.7 | 87 | 15.9 |
| 8.6 | 103 | 18.9 |

TABLE 16-continued

| Form XIII | | |
|---|---|---|
| 2-Theta (°) | Height | H % |
| 9.8 | 71 | 13.0 |
| 11.8 | 359 | 65.8 |
| 12.6 | 163 | 29.9 |
| 13.4 | 142 | 26.0 |
| 14.1 | 506 | 92.7 |
| 14.8 | 546 | 100 |
| 16.6 | 182 | 33.3 |
| 17.9 | 54 | 9.9 |
| 19.1 | 489 | 89.6 |
| 19.4 | 169 | 31.0 |
| 19.9 | 67 | 12.3 |
| 20.9 | 82 | 15.0 |
| 21.4 | 147 | 26.9 |
| 22.4 | 362 | 66.3 |
| 23.2 | 81 | 14.8 |
| 24.0 | 128 | 23.4 |
| 24.9 | 386 | 70.7 |
| 26.3 | 245 | 44.9 |
| 28.4 | 44 | 8.1 |
| 28.8 | 78 | 14.3 |
| 29.8 | 47 | 8.6 |
| 30.8 | 216 | 39.6 |
| 33.2 | 36 | 6.6 |
| 34.9 | 36 | 6.6 |

TABLE 17

| Form XIV | | |
|---|---|---|
| 2-Theta (°) | Height | H % |
| 4.0 | 1030 | 100 |
| 5.7 | 80 | 7.8 |
| 8.0 | 76 | 7.4 |
| 8.7 | 33 | 3.2 |
| 9.8 | 38 | 3.7 |
| 11.2 | 932 | 90.5 |
| 11.9 | 335 | 32.5 |
| 12.7 | 38 | 3.7 |
| 13.4 | 37 | 3.6 |
| 14.1 | 350 | 34 |
| 14.8 | 277 | 26.9 |
| 15.9 | 623 | 60.5 |
| 16.6 | 166 | 16.1 |
| 17.0 | 107 | 10.4 |
| 17.9 | 56 | 5.4 |
| 19.1 | 308 | 29.9 |
| 19.5 | 147 | 14.3 |
| 19.8 | 147 | 14.3 |
| 21.0 | 194 | 18.8 |
| 21.4 | 70 | 6.8 |
| 21.9 | 38 | 3.7 |
| 22.4 | 173 | 16.8 |
| 23.3 | 61 | 5.9 |
| 24.0 | 111 | 10.8 |
| 24.4 | 115 | 11.2 |
| 24.9 | 349 | 33.9 |
| 26.3 | 129 | 12.5 |
| 27.2 | 35 | 3.4 |
| 28.1 | 109 | 10.6 |
| 28.5 | 64 | 6.2 |
| 28.9 | 94 | 9.1 |
| 29.9 | 65 | 6.3 |
| 30.9 | 100 | 9.7 |
| 32.1 | 38 | 3.7 |
| 33.2 | 59 | 5.7 |
| 35.6 | 34 | 3.3 |
| 43.5 | 31 | 3.0 |

TABLE 18

| Form XV | | |
|---|---|---|
| 2-Theta (°) | Height | H % |
| 7.4 | 192 | 6.3 |
| 7.9 | 113 | 3.7 |
| 9.6 | 203 | 6.6 |
| 12.4 | 283 | 9.2 |
| 13.4 | 923 | 30.2 |
| 15.5 | 3060 | 100 |
| 16.9 | 230 | 7.5 |
| 17.7 | 1713 | 56.0 |
| 19.0 | 628 | 20.5 |
| 19.5 | 881 | 28.8 |
| 20.6 | 1070 | 35.0 |
| 21.9 | 554 | 18.1 |
| 22.5 | 2295 | 75.0 |
| 23.8 | 401 | 13.1 |
| 24.3 | 444 | 14.5 |
| 24.7 | 382 | 12.5 |
| 25.4 | 707 | 23.1 |
| 26.2 | 79 | 2.6 |
| 26.8 | 1049 | 34.3 |
| 28.1 | 655 | 21.4 |
| 29.0 | 578 | 18.9 |
| 30.0 | 144 | 4.7 |
| 30.5 | 331 | 10.8 |
| 31.1 | 328 | 10.7 |
| 31.5 | 483 | 15.8 |
| 32.3 | 66 | 2.2 |
| 33.8 | 217 | 7.1 |
| 34.1 | 159 | 5.2 |
| 35.4 | 172 | 5.6 |
| 36.0 | 205 | 6.7 |
| 37.0 | 66 | 2.2 |
| 38.1 | 188 | 6.1 |
| 39.8 | 145 | 4.7 |
| 40.7 | 143 | 4.7 |
| 42.3 | 268 | 8.8 |
| 42.7 | 183 | 6.0 |
| 43.4 | 81 | 2.6 |
| 43.8 | 90 | 2.9 |

Example 7. DSC and TGA Studies of Polymorphic Forms

DSC studies were carried out on Forms Va, VII, VIII, X, XII, XIII, XIV, and XV. The DSC was obtained from TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

TGA studies were carried out on Forms Va, VII, VIII, X, XIII, and XV. The TGA was obtained from TA Instrument Thermogravimetric Analyzer, Model Q500. The general experimental conditions for TGA were: ramp from 20° C. to 600° C. at 20° C./min; nitrogen purge, gas flow at 40 mL/min followed by balance of the purge flow; sample purge flow at 60 mL/min; platinum sample pan.

Table 19 below shows the results for DSC and TGA.

TABLE 19

| Form | DSC | TGA |
|---|---|---|
| Va | a minor endothermic event at an onset temperature of 130° C. with a peak temperature of 133° C.; a major endothermic event at an onset temperature of 266° C. with a peak temperature of 267° C. | a weight loss of about 0.3% up to 100° C.; significant weight loss above 300° C. |
| VII | an endothermic event at an onset temperature and peak temperature of 126° C.; an endothermic event at an onset temperature of 255° C. with a peak temperature of 256° C.; an exothermic event at peak temperature of 260° C.; an endothermic event at an onset temperature of 266° C. with a peak temperature of 267° C. | a weight loss of about 8% up to 120° C.; significant weight loss above 300° C. |
| VIII | a minor endothermic event at an onset temperature of 128° C. with a peak temperature of 145° C.; a major endothermic event at an onset temperature of 262° C. with a peak temperature of 265° C. | a weight loss of about 14% up to 140° C.; significant weight loss above 300° C. |
| X | a minor endothermic event at an onset temperature of 117° C. with a peak temperature of 121° C.; a major endothermic event at an onset temperature of 266° C. with a peak temperature of 267° C. | a weight loss of about 8% up to 120° C.; significant weight loss above 300° C. |
| XII | an endothermic event at an onset temperature of 261° C. with a peak temperature of 264° C. | NA |
| XIII | an endothermic event at an onset temperature of 266° C. with a peak temperature of 267° C. | a weight loss of about 2% up to 140° C.; significant weight loss above 300° C. |
| XIV | an endothermic event at an onset temperature of 266° C. with a peak temperature of 267° C. | NA |
| XV | an endothermic event at an onset temperature of 57° C. with a peak temperature of 85° C.; an endothermic event at an onset temperature of 164° C. with a peak temperature of 172° C.; an exothermic event at an onset temperature of 183° C. with a peak temperature of 192° C.; a major endothermic event at an onset temperature of 267° C. with a peak temperature of 268° C. | a weight loss of about 0.4% up to 150° C.; significant weight loss above 300° C. |

NA: not available

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A solid form of a compound having the formula:

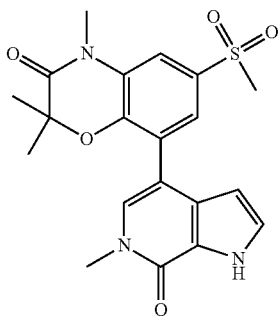

Compound 1 wherein the solid form is crystalline;
and wherein the solid form has Form I and has a characteristic XRPD peak, in terms of 2-theta, at about 12.7 degrees.

2. The solid form of claim 1 which is an anhydrate.

3. The solid form of claim 1, further having two or more characteristic XRPD peaks, in terms of 2-theta, selected from about 8.7, about 9.8, about 11.6, about 14.7, about 15.7, about 20.0, about 21.4, about 23.3, and about 27.1 degrees.

4. The solid form of claim 1 having an XRPD pattern substantially as shown in FIG. 1.

5. The solid form of claim 1 having a DSC thermogram characterized by an endothermic peak at a temperature of about 266° C.

6. The solid form of claim 1 having a DSC thermogram substantially as shown in FIG. 2.

7. The solid form of claim 1 having a TGA thermogram substantially as shown in FIG. 3.

8. A solid form of a compound having the formula:

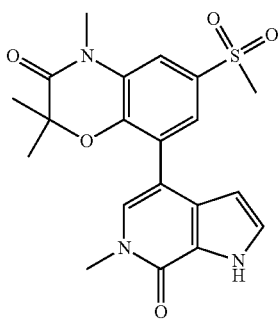

Compound 1 wherein the solid form is crystalline;
and wherein the solid form has Form II and has a characteristic XRPD peak, in terms of 2-theta, at about 17.0 degrees.

9. The solid form of claim 8, further having two or more characteristic XRPD peaks, in terms of 2-theta, selected from about 6.7, about 9.5, about 10.5, about 14.8, about 16.2, about 18.8, and about 19.3 degrees.

10. The solid form of claim 8 having an XRPD pattern substantially as shown in FIG. 4.

11. The solid form of claim 8 having a DSC thermogram characterized by an endothermic peak at a temperature of about 268° C.

12. The solid form of claim 8 having a DSC thermogram substantially as shown in FIG. 5.

13. The solid form of claim 8 having a TGA thermogram substantially as shown in FIG. 6.

14. A pharmaceutical composition comprising a solid form of claim 1 and at least one pharmaceutically acceptable carrier.

15. A process of preparing Form I of Compound 1:

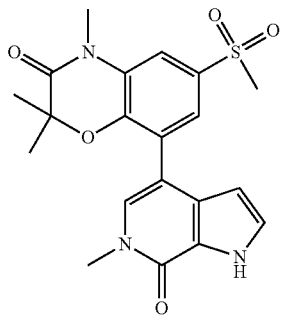

Compound 1 comprising precipitating Form I from a solution comprising Compound 1 and a solvent.

16. The process of claim 15, wherein the solvent comprises methanol, acetone, n-heptane, or a mixture thereof.

17. The process of claim 15, wherein the precipitating is carried out by (1) reducing the temperature of the solution of Compound 1, (2) concentrating the solution of Compound 1, (3) adding an anti-solvent to the solution of Compound 1, or (4) any combination thereof.

18. The process of claim 15, wherein the preparation of Form I comprises:

(ia) heating the solution of Compound 1 to a temperature of about 50° C. to about 60° C.;

(iia) reducing the volume of the solution of Compound 1 at the temperature of about 50° C. to about 60° C. to form a reduced-volume solution of Compound 1;

(iiia) adding an anti-solvent to the reduced-volume solution of Compound 1 while maintaining the temperature at about 55° C. to about 65° C. to form a warm solution of Compound 1; and (iva) cooling the warm solution of Compound 1 to a temperature of about 15° C. to about 30° C. to precipitate Form I.

19. The process of claim 15, wherein the preparation of Form I comprises:

(ib) heating the solution of Compound 1, wherein the solution comprises methanol and acetone as solvent, to a temperature of about 50° C. to about 60° C.;

(iib) reducing the volume of the solution of Compound 1 at the temperature of about 50° C. to about 60° C. to form a reduced-volume solution of Compound 1;

(iiib) adding n-heptane to the reduced-volume solution of Compound 1 while maintaining the temperature at about 55° C. to about 65° C. to form a warm solution of Compound 1; and (ivb) cooling the warm solution of Compound 1 to a temperature of about 15° C. to about 30° C. to precipitate Form I.

20. A process of preparing Form II of Compound 1:

Compound 1 comprising precipitating Form II from a solution comprising Compound I and a solvent.

21. The process of claim 20, wherein the solvent comprises tetrahydrofuran (THF), acetone, n-heptane, or a mixture thereof.

22. The process of claim 20, wherein the precipitating is carried out by (1) reducing the temperature of the solution of Compound 1, (2) concentrating the solution of Compound 1, (3) adding an anti-solvent to the solution of Compound 1, or (4) any combination thereof.

23. The process of claim 20, wherein the preparation of Form II comprises:
   (ic) heating the solution of Compound 1 to a temperature of about 50° C. to about 60° C.;
   (iic) reducing the volume of the solution of Compound 1 at the temperature of about 50° C. to about 60° C. to form a reduced-volume solution of Compound 1;
   (iiic) adding an anti-solvent to the reduced-volume solution of Compound 1 while maintaining the temperature at about 55° C. to about 65° C. to form a warm solution of Compound 1; and
   (ivc) cooling the warm solution of Compound 1 to a temperature of about 15° C. to about 30° C. to precipitate Form II.

24. The process of claim 15 further comprising preparing Compound 1, or a salt thereof, by a process comprising reacting Compound 8:

Compound 8 with B1, wherein B1 is a base.

25. The process of claim 24, wherein B1 is an alkali metal hydroxide base.

26. The process of claim 24, wherein the reacting of Compound 8 with B1 is carried out in a first solvent.

27. The process of claim 24 further comprising preparing Compound 8 by a process comprising reacting Compound 7:

Compound 7 with Compound 9:

Compound 9 in the presence of P2 and B2, wherein P2 is a transition metal catalyst and B2 is a base.

28. A process of preparing Compound 8:

Compound 8 comprising reacting Compound 7:

Compound 7 with Compound 9:

Compound 9 in the presence of P2 and B2, wherein P2 is a transition metal catalyst and B2 is a base.

29. The process of claim 27, wherein P2 is a palladium catalyst.

30. The process of claim 27, wherein B2 is an alkali metal bicarbonate base.

31. The process of claim 27, wherein the reacting of Compound 7 with Compound 9 is carried out in a second solvent.

32. The process of claim 27 further comprising preparing Compound 7 by a process comprising reacting Compound 6:

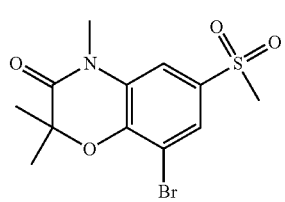

Compound 6 with 4,4,4',4',5,5,5',5'-octamethyl-2,2'-bi(1,3,2-dioxaborolane) in the presence of P3 and B3, wherein P3 is a transition metal catalyst and B3 is a base.

33. The solid form of claim 1, further having one or more characteristic XRPD peaks, in terms of 2-theta, selected from about 8.7, about 9.8, about 21.4, and about 23.3 degrees.

34. The solid form of claim 1, further having one or more characteristic XRPD peaks, in terms of 2-theta, selected from about 8.7, about 9.8, about 11.6, about 14.7, about 15.7, about 20.0, about 21.4, about 23.3, and about 27.1 degrees.

35. The solid form of claim 1, further having three or more characteristic XRPD peaks, in terms of 2-theta, selected from about 8.7, about 9.8, about 11.6, about 14.7, about 15.7, about 20.0, about 21.4, about 23.3, and about 27.1 degrees.

36. The solid form of claim 8, further having one or more characteristic XRPD peaks, in terms of 2-theta, selected from about 6.7, about 9.5, about 10.5, about 14.8, about 16.2, about 18.8, and about 19.3 degrees.

37. The solid form of claim 8, further having three or more characteristic XRPD peaks, in terms of 2-theta, selected from about 6.7, about 9.5, about 10.5, about 14.8, about 16.2, about 18.8, and about 19.3 degrees.

38. A pharmaceutical composition comprising a solid form of claim 8 and at least one pharmaceutically acceptable carrier.

* * * * *